United States Patent
Gong et al.

(10) Patent No.: US 9,896,682 B2
(45) Date of Patent: Feb. 20, 2018

(54) STABILIZED RNA SOLUTIONS

(71) Applicant: Bio-Rad Laboratories, Inc., Hercules, CA (US)

(72) Inventors: Xiao-Song Gong, Richmond, CA (US); Cindy Wan, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/063,139

(22) Filed: Mar. 7, 2016

(65) Prior Publication Data

US 2016/0257950 A1    Sep. 8, 2016

Related U.S. Application Data

(60) Provisional application No. 62/129,625, filed on Mar. 6, 2015.

(51) Int. Cl.
C12N 15/10 (2006.01)
C12N 9/22 (2006.01)

(52) U.S. Cl.
CPC ........... C12N 15/1003 (2013.01); C12N 9/22 (2013.01); *C12Y 301/00* (2013.01)

(58) Field of Classification Search
None
See application file for complete search history.

(56) References Cited

U.S. PATENT DOCUMENTS

| | | | |
|---|---|---|---|
| 4,386,202 A | 5/1983 | Nelson | |
| 4,683,195 A | 7/1987 | Mullis et al. | |
| 6,204,375 B1 | 3/2001 | Lader | |
| 6,528,641 B2 | 3/2003 | Lader | |
| 6,627,398 B1 | 9/2003 | Wilusz et al. | |
| 8,088,602 B1 | 1/2012 | Frayne | |
| 8,178,296 B2 | 5/2012 | Lader | |
| 8,460,684 B2 | 6/2013 | Raines et al. | |
| 2001/0051715 A1 | 12/2001 | Taylor et al. | |
| 2002/0026046 A1 | 2/2002 | Pasloske et al. | |
| 2002/0115851 A1* | 8/2002 | Korfhage ........... | C12N 15/1003 536/25.4 |
| 2010/0099149 A1 | 4/2010 | Birnboim et al. | |
| 2011/0318811 A1 | 12/2011 | Latham et al. | |
| 2012/0052572 A1 | 3/2012 | Whitney et al. | |
| 2013/0209997 A1 | 8/2013 | Whitney et al. | |
| 2013/0344536 A1 | 12/2013 | Sevastsyanovich et al. | |
| 2013/0344563 A1 | 12/2013 | Raines et al. | |
| 2014/0154783 A1 | 6/2014 | Rossomando et al. | |
| 2014/0295404 A1 | 10/2014 | Goldsborough et al. | |
| 2014/0295411 A1 | 10/2014 | Lader | |

FOREIGN PATENT DOCUMENTS

| | | |
|---|---|---|
| WO | 2010083844 A1 | 7/2010 |
| WO | 2012075471 A1 | 6/2012 |

OTHER PUBLICATIONS

Eastlund, E. and Mueller, E. 2001. Hot Start RT-PCR results in improved performance of the enhanced avian RT-PCR system. LifeScience Quarterly 2:2-5.*
DNase I Demystified:Ambions TechNotes Newsletter, 2001, 8:4, pp. 1-3—Retrieved from < https://www.tamu.edu/faculty/riggs/BIOT602/Ambion_DNase%20I%20Demystified.pdf > on Oct. 25, 2016.*
Sigma aroduct Information, "DNase I recombinant, RNase-free", 2008. < http://www.sigmaaldrich.com/content/dam/sigma-aldrich/docs/Roche/Bulletin/1/04716728001bul.pdf > Retrieved on Oct. 25, 2016.*
Bachoon et al., "DNAse removal in RNA isolation and RT-PCR DNAse removal in RNA isolation and RT-PCR", FEMS Microbiology Letters, 2001, vol. 201, 127-132.*
RN Easy Handbook, Qiagen, 2001. Retrieved from < https://www.arabidopsis.org/download_files/Protocols/RNeasy.pdf > on Apr. 7, 2017.*
Huang et al., "Optimization of DNase I Removal of Contaminating DNA from RNA for Use in Quantitative RNA-PCR" BioTechniques, 1996, vol. 20, pp. 1012-1020.*
Chomczynski. "Single-Step Method of RNA Isolation by Acid Guanidinium Thiocyanate-Phenol-Chloroform Extraction", Analytical Biochemistry. Apr. 1987, vol. 162, No. 1, pp. 156-159.
Li, et al., "Kinetics of RNA Degradation by Specific Base Catalysis of Transesterification Involving the 2'-Hydroxyl Group" J. Am. Chem. Soc., 1999, vol. 121, pp. 5364-5372.
Sambrook, "Enzymatic Manipulation of DNA and RNA," In: Sambrook J., Ressell D.W. (Eds.), Molecular Cloning—a laboratory manual, $2^{nd}$ edition, Cold Spring Harbor Laboratory Press, Cold Spring Harbor, 1989.
Sambrook, "Preparation and Analysis of RNA," In: Sambrook J., Ressell D.W. (Eds.), Molecular Cloning—a laboratory manual, $2^{nd}$ edition, Cold Spring Harbor Laboratory Press, Cold Spring Harbor, 1989.
Sambrook, "The Polymerase Chain Reaction," In: Sambrook J., Ressell D.W. (Eds.), Molecular Cloning—a laboratory manual, $2^{nd}$ edition, Cold Spring Harbor Laboratory Press, Cold Spring Harbor, 1989.

* cited by examiner

*Primary Examiner* — Suzanne M Noakes
(74) *Attorney, Agent, or Firm* — Kilpatrick Townsend & Stockton LLP

(57) ABSTRACT

Methods and compositions are described herein for protecting RNA from autocatalytic and divalent cation induced degradation in an aqueous solution.

23 Claims, 3 Drawing Sheets

US 9,896,682 B2

STABILIZED RNA SOLUTIONS

CROSS-REFERENCES TO RELATED APPLICATIONS

This application claims priority to U.S. Provisional Application No. 62/129,625, filed Mar. 6, 2015, the contents of which are hereby incorporated by reference in the entirety for all purposes.

BACKGROUND OF THE INVENTION

Ribonucleic acid (RNA) is useful in a variety of applications, including cDNA library construction and the analysis of gene expression via sequencing, digital amplification, northern blotting, microarray hybridization, or RT-PCR. Each of these applications typically requires storage or handling of the RNA in an aqueous solution phase. However, RNA is naturally unstable in aqueous solution, and care must be taken to ensure that the quality of an RNA sample is sufficiently maintained for these applications. For example, care must be taken to protect RNA from degradation by RNase enzymes. Additionally, RNA can degrade through a variety of enzyme-independent mechanisms, including autocatalytic degradation. In some cases, compounds or conditions necessary for downstream processing of the RNA can increase RNA degradation. For example, the presence of free or chelated divalent cations in the solution can increase the degradation of RNA via enzymatic or non-enzymatic mechanisms, yet such divalent cations can be necessary to achieve desired enzyme catalysis and/or hybridization reactions. As another example, heat can also increase the degradation of RNA via enzymatic or non-enzymatic mechanisms, yet such heat can be a necessary component of an RNA analysis method.

BRIEF SUMMARY OF THE INVENTION

In one aspect, the present invention provides a method of protecting RNA from degradation in an aqueous solution, said method comprising: —providing a solution comprising: i. water; ii. RNA; iii. divalent cations; and iv. a phosphorous-containing or a sulfur-containing compound; and —incubating the provided solution at a temperature of at least 25° C., 37° C., 40° C., 50° C., 55° C., 60° C., 65° C., 70° C., or 75° C., wherein the RNA is protected from degradation as compared to an RNA in an aqueous solution that contains the divalent cations but does not contain the phosphorous-containing or sulfur-containing compound.

In some embodiments, the providing comprises purifying RNA from a cell or tissue. In some cases, the purified RNA is free or substantially free of endogenous host proteins from the cell or tissue. In some embodiments, the RNA is at a concentration of from 0.1 pg/mL to 500 µg/mL. In some embodiments, the provided solution further comprises a DNase enzyme. In some cases, the DNase enzyme is at a concentration of from 0.01 U/µL to 0.2 U/µL. In some cases, the RNA is from a cell or tissue, and the DNase enzyme is exogenous or heterologous to the cell or tissue from which the RNA is derived. In some cases, the DNase enzyme is a recombinant DNase enzyme. In some cases, the recombinant DNase enzyme is recombinant bovine pancreas DNase I.

In some cases, before the incubating the provided solution at a temperature of at least 37° C., 40° C., 50° C., 55° C., 60° C., 65° C., 70° C., or 75° C., the method comprises incubating the provided solution under conditions suitable for performing a DNase reaction. In some cases, before the incubating the provided solution under conditions suitable for performing the DNase reaction, the provided solution comprises DNA and the DNase reaction degrades the DNA. In some cases, the mass of the DNA in the provided solution is 30% or less of the mass of the RNA in the provided solution. In some cases, the DNA in the provided solution before the DNase reaction is performed is at a concentration of less than 50 ng/µL. In some cases, the DNA is genomic DNA. In some cases, the genomic DNA is derived from a cell or tissue and the RNA is derived from the same cell or tissue.

In some embodiments, the method comprises incubating the provided solution at a temperature of at least 55° C., 58° C., 60° C., 65° C., 70° C., or 75° C., and the incubating the provided solution at a temperature of at least 55° C., 58° C., 60° C., 65° C., 70° C., or 75° C. inactivates the DNase enzyme. In some embodiments, after incubating the provided solution at a temperature of at least 55° C., 58° C., 60° C., 65° C., 70° C., or 75° C., the method comprises quantifying the RNA in the provided solution.

In some embodiments, the incubating the provided solution at a temperature of at least 55° C., 58° C., 60° C., 65° C., 70° C., or 75° C. comprises incubating the provided solution at a temperature of between about 55° C. and about 110° C., between about 55° C. and about 100° C., between about 55° C. and about 99° C., between about 55° C. and about 95° C., between about 55° C. and about 90° C., between about 55° C. and about 85° C., between about 55° C. and about 80° C., between about 55° C. and about 75° C., between about 55° C. and about 70° C., between about 55° C. and about 65° C., between about 55° C. and about 60° C., between about 60° C. and about 110° C., between about 60° C. and about 100° C., between about 60° C. and about 99° C., between about 60° C. and about 95° C., between about 60° C. and about 90° C., between about 60° C. and about 85° C., between about 60° C. and about 80° C., between about 60° C. and about 75° C., between about 60° C. and about 70° C., between about 60° C. and about 65° C., between about 65° C. and about 110° C., between about 65° C. and about 100° C., between about 65° C. and about 99° C., between about 65° C. and about 95° C., between about 65° C. and about 90° C., between about 65° C. and about 85° C., between about 65° C. and about 80° C., between about 65° C. and about 75° C., or between about 65° C. and about 70° C.

In some cases, the method provides a greater accuracy of quantitation as compared to quantitation of RNA in an aqueous solution that contains the divalent cations but does not contain the phosphorous-containing or sulfur-containing compound.

In some cases, the quantifying comprises contacting the RNA, or a portion thereof, with a reverse transcriptase, thereby reverse transcribing the RNA or portion thereof, into cDNA. In some cases, during or after the reverse transcription, the RNA is degraded by RNase H. In some cases, the reverse transcriptase that transcribes the RNA, or portion thereof, into cDNA comprises the RNase H. In some cases, the RNase H is a structurally different enzyme than the reverse transcriptase that transcribes the RNA, or portion thereof, into cDNA. In some cases, before the contacting the RNA, or a portion thereof, with a reverse transcriptase, the provided solution is RNase free or substantially RNase free. In some cases, after the reverse transcription, the method further comprises amplifying at least a portion of the reverse transcribed cDNA. In some cases, the method further comprises monitoring the amplification reaction in real time. In some cases, the quantifying comprises contacting the RNA, a portion thereof, or a reverse transcriptase-mediated product of the RNA or a portion thereof with complementary nucleic acid. In some cases, the complementary nucleic acid is immobilized on a solid surface (e.g., immobilized in a flow cell or on a microarray). In some cases, the complementary nucleic acid comprises one or more oligonucleotide primers.

In some embodiments, the phosphorous-containing or sulfur-containing compound is selected from the group consisting of phosphate, glycerol phosphate, glucose phosphate, ribose phosphate, pyrophosphate, and polyphosphate. In some embodiments, the phosphorous-containing or sulfur-containing compound is sulfate. In some embodiments, the phosphorous-containing or sulfur-containing compound is at a concentration of from 0.1 mM to 500 mM. In some embodiments, the phosphorous-containing or sulfur-containing compound is at a concentration of 5 mM. In some cases, the phosphorous-containing or sulfur-containing compound is heterologous to the RNA. In some embodiments, the divalent cations are or comprise divalent calcium cations. In some cases, the calcium is at a concentration of from 10 µM to 1 mM.

In some embodiments, the divalent cations are or comprise magnesium cations. In some cases, the magnesium is at a concentration of from 0.1 mM to 10 mM. In some embodiments, the provided solution comprises two chemically distinct divalent cations. In some cases, the two chemically distinct divalent cations are magnesium cations and calcium cations. In some cases, the calcium is at a concentration of from 10 µM to 1 mM and the magnesium is at a concentration of from 0.1 mM to 10 mM.

In another aspect, the present invention provides an aqueous solution comprising: i. water; ii. RNA; iii. divalent cations; and iv. a phosphorous-containing or a sulfur-containing compound, wherein the RNA is protected from degradation as compared to an RNA in an aqueous solution that contains the divalent cations but does not contain the phosphorous-containing or sulfur-containing compound. In some embodiments, the solution is compatible with reverse transcription of the RNA into cDNA. In some embodiments, the solution is configured to provide a more accurate quantitation of a concentration of the RNA in the solution as compared to an RNA in an aqueous solution that contains the divalent cations but does not contain the phosphorous-containing or sulfur-containing compound. In some embodiments, the RNA is at a concentration of from 0.1 pg/mL to 500 µg/mL. In some embodiments, the RNA is purified from a cell or tissue. In some cases, the purified RNA is free or substantially free of endogenous host proteins from the cell or tissue.

In some embodiments, the solution further comprises a DNase enzyme. In some cases, the DNase enzyme is at a concentration of from 0.01 U/µL to 0.2 U/µL. In some cases, the RNA is from a cell or tissue, and the DNase enzyme is exogenous or heterologous to the cell or tissue from which the RNA is derived. In some cases, the DNase enzyme is a recombinant DNase enzyme. In some cases, the recombinant DNase enzyme is bovine pancreas DNase I. In some cases, the DNase enzyme is a heat-inactivated DNase enzyme. In some cases, the solution comprises heat-inactivated DNase enzyme at a concentration corresponding to 0.01 U/µL to 0.2 U/µL of active DNase enzyme.

In some embodiments, the solution further comprises DNA. In some cases, the DNA is genomic DNA. In some cases the DNA is DNase digested, e.g., digested by a DNase (e.g., recombinant and/or heterologous DNase) enzyme. In some cases, the mass of the DNA in the solution is 30% or less of the mass of the RNA in the solution. In some cases, the DNA in the solution is at a concentration of less than 50 ng/µL. In some cases, the genomic DNA is derived from a cell or tissue and the RNA is derived from the same cell or tissue.

In some embodiments, the solution is at a temperature of at least 25° C., 37° C., 40° C., 50° C., 55° C., 60° C., 65° C., 70° C., or 75° C. In some embodiments, the solution is at a temperature of between about 25° C. and about 110° C., between about 25° C. and about 100° C., between about 25° C. and about 99° C., between about 25° C. and about 95° C., between about 25° C. and about 90° C., between about 25° C. and about 85° C., between about 25° C. and about 80° C., between about 25° C. and about 75° C., between about 25° C. and about 70° C., between about 25° C. and about 65° C., between about 25° C. and about 60° C., between about 25° C. and about 55° C., between about 30° C. and about 110° C., between about 30° C. and about 100° C., between about 30° C. and about 95° C., between about 30° C. and about 90° C., between about 30° C. and about 85° C., between about 30° C. and about 80° C., between about 30° C. and about 75° C., between about 30° C. and about 70° C., between about 30° C. and about 65° C., between about 40° C. and about 110° C., between about 40° C. and about 100° C., between about 40° C. and about 95° C., between about 40° C. and about 90° C., between about 40° C. and about 85° C., between about 40° C. and about 80° C., between about 40° C. and about 75° C., between about 40° C. and about 70° C., or between about 40° C. and about 65° C.

In some embodiments, the solution further comprises an oligonucleotide nucleic acid amplification primer and dNTPs. In some embodiments, the solution further comprises a pair of oligonucleotide amplification primers. In some embodiments, the solution further comprises a reverse transcriptase enzyme. In some embodiments, the solution further comprises a DNA-dependent DNA polymerase (e.g., a recombinant DNA-dependent DNA polymerase and/or a DNA-dependent DNA polymerase that is exogenous or heterologous with respect to the RNA). In some embodiments, the phosphorous-containing or sulfur-containing compound is selected from the group consisting of phosphate, glycerol phosphate, glucose phosphate, ribose phosphate, pyrophosphate, and polyphosphate. In some embodiments, the phosphorous-containing or sulfur-containing compound is heterologous with respect to the RNA.

In some embodiments, the phosphorous-containing or sulfur-containing compound is sulfate. In some embodiments, the phosphorous-containing or sulfur-containing compound is at a concentration of from 0.1 mM to 500 mM. In some embodiments, the phosphorous-containing or sulfur-containing compound is at a concentration of 5 mM. In some embodiments, the divalent cations are calcium cations. In some cases, the calcium is at a concentration of from 10 µM to 1 mM. In some cases, the divalent cations are magnesium cations. In some cases, the magnesium is at a concentration of from 0.1 mM to 10 mM.

In some embodiments, the solution comprises two chemically distinct divalent cations. In some embodiments, the two chemically distinct divalent cations are magnesium cations and calcium cations. In some cases, the calcium is at a concentration of from 10 µM to 1 mM and the magnesium is at a concentration of from 0.1 mM to 10 mM. In some embodiments, the solution is RNase free.

DEFINITIONS

Figure 1A:
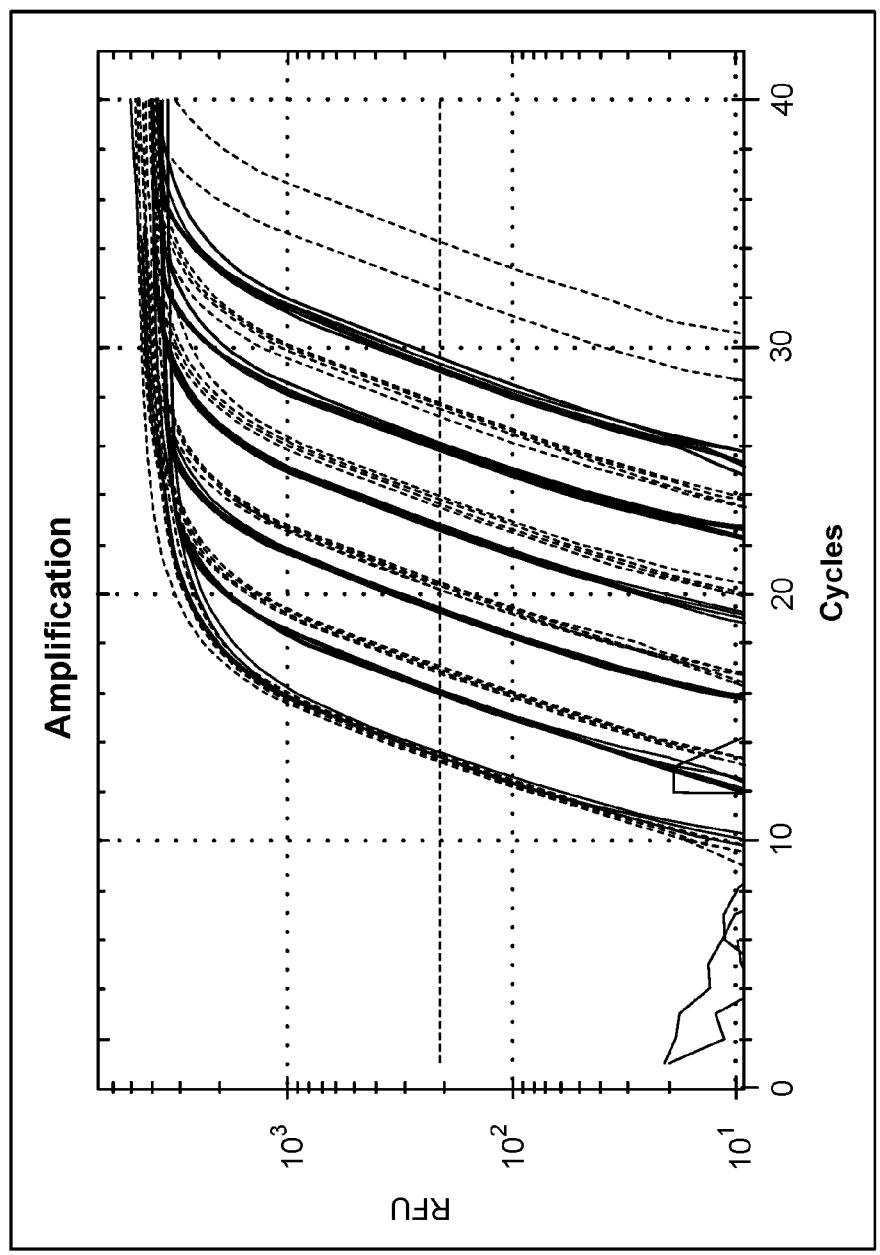
FIG. 1A: depicts real-time amplification results from a cDNA template derived from an RNA sample that is subject to various conditions. Heating an aqueous solution containing RNA to 75° C. in the presence of $MgCl_2$ and $CaCl_2$ and without phosphorous or sulfur containing compounds results in severe Cq delay as compared to a sample that is not heat treated, especially at lower RNA inputs.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthesis described below are those well-known and commonly employed in the art. Standard techniques, or modifications thereof, are used for chemical syntheses and chemical analyses.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety. Nucleotides, may be referred to by their commonly accepted single-letter codes.

As used herein, the term "RNA" refers to ribonucleic acid, and any chemical modifications thereof, with the exception of a chemical modification rendering the RNA into DNA. The RNA can be single-stranded, or double stranded, or a more highly aggregated form. The RNA can be provided by any means known in the art, including but not limited to, in vitro transcription, purification from an organism, chemical synthesis, or a combination thereof. The RNA can be, but is not limited to, mRNA, rRNA, tRNA, microRNA, or total RNA. The RNA can be purified RNA (e.g., purified mRNA, purified rRNA, purified tRNA, purified microRNA, or purified total RNA).

As used herein, "protecting RNA from degradation" refers to increasing the stability of the RNA in solution. Stability, in the context of ribonucleic acid (RNA) refers to the ability of the RNA to be resistant to enzymatic, autocatalytic, metal-catalyzed, or pH dependent degradation in solution, or a combination thereof. The ability of a composition, reaction mixture, or method to increase the stability of RNA can be determined by comparison of the stabilized RNA to RNA in solution that is not treated with a method or composition for increasing stability as described herein, or is not in a reaction mixture for increasing stability as described herein. Such comparison can be performed by an assay of the RNA or a cDNA product thereof, such as, e.g., a reverse-transcriptase amplification assay (e.g., RT-PCR), a microarray assay, high-throughput sequencing, electrophoresis (e.g., gel or capillary electrophoresis), or spectrometry (e.g., mass spectrometry).

As used herein, the phrase "free of endogenous host proteins" refers to RNA that has been purified away from protein components of a host organism, cell, or tissue, from which the RNA has been extracted, or a reaction mixture containing RNA that has been purified away from protein components of a host organism from which the RNA has been extracted. One of skill in the art will appreciate that such RNA, or reaction mixtures containing such RNA, can have a small amount of endogenous host proteins detectable using extremely sensitive methods. Generally, however, such RNA, or reaction mixtures containing such RNA, are at least, or at least about, 90%, 95%, 99%, 99.9%, 99.999% or more free of endogenous host proteins (e.g., w/w).

As used herein, the term "RNase free" refers to a composition, solution, or reaction mixture, that lacks, or substantially lacks, detectable RNase activity. In some cases, the composition, solution, or reaction mixture is rendered RNase free by use of an RNase inhibitor, e.g., SUPERase•In™, RNase OUT™, ANTI-RNASE, RNAsecure™, or human placental RNase Inhibitor (available from New England Biolabs). In some cases, the composition, solution, or reaction mixture is rendered RNase free by use of a protein modification agent, such as diethylpyrocarbonate. One of skill in the art will appreciate that despite good laboratory practice, solutions or reaction mixtures can have a small amount of contaminating RNase activity that is detectable using extremely sensitive methods. Generally, however, such solutions or reaction mixtures have a contamination level of less than about 1 pg/μL, 0.1 pg/μL, 0.01 pg/μL, 0.001 pg/μL, or 0.0001 pg/μL active RNase. As such, RNase free solutions or reaction mixtures have a contamination level of less than about 0.001, 0.0001, 0.00001, or 0.000001 units of RNase activity.

As used herein, the term "DNase reaction" refers to a method of incubating a solution containing DNase (e.g., recombinant and/or heterologous DNase) under conditions sufficient to degrade or eliminate DNA oligonucleotides in the solution having a length greater than 3 nucleotides. Such conditions can include incubating the DNase containing solution at a temperature of about, or of at least about, 20° C., 25° C., or 37° C. In some cases, such conditions can include incubating the DNase containing solution at a temperature of, or of at least about, 25° C., or 37° C. In some cases, such conditions can include incubating the DNase containing solution at a temperature of about, or of at least about, 37° C. In some cases, such conditions include incubating the DNase in a DNase containing solution that also contains calcium or calcium and magnesium divalent cations. In some cases, such conditions include incubating the DNase in a DNase containing solution that also contains sufficient calcium and/or magnesium divalent cations for efficient (e.g., optimal) DNase activity.

The term "nucleic acid amplification," "amplification reaction," or "amplifying" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3 SR) amplification reactions as well as others known to those of skill in the art.

As used herein, the term "heterologous" refers two elements that are not found together in nature. For example, a DNase I enzyme that is heterologous to an RNA can refer to an RNA purified from a cell, tissue, or organism and a DNase I enzyme that is purified from a different source (e.g., a recombinant DNase I enzyme purified from a cell or tissue of a different organism.

DETAILED DESCRIPTION OF THE INVENTION

I. Introduction

Compositions, methods, and kits for the preparation, purification, storage, and analysis of ribonucleic acid (RNA) are widely used throughout various fields of biology and biotechnology. In solution, RNA is generally significantly less stable than its deoxyribonucleic (DNA) counterpart. This lack of stability arises from several different phenomena. For example, RNase enzymes are ubiquitous in the environment, and highly stable and processive. Thus, RNase contamination can contribute to the destabilization of RNA in solution. RNase contamination can be mitigated or eliminated by use of RNase free supplies, RNase inhibitors, and good laboratory practices.

The stability of RNA in solution can also be decreased by autocatalytic and metal catalyzed mechanisms of RNA degradation. Although metal-catalyzed degradation can be at least partly mitigated by chelating free metals in the solution under certain conditions, in some cases metal catalyzed RNA degradation can be exacerbated by use of metal chelating compounds. Autocatalytic or metal catalyzed degradation mechanisms can also be at least partially mitigated by keeping the RNA solution at a low temperature (e.g., 8° C., 6° C., 4° C., or less). However, such low temperatures can be incompatible with one or more analysis steps, such as in vitro transcription, RNA amplification, in vitro translation of the RNA, DNase digestion of the RNA to remove any contaminating DNA, heat inactivation of the DNase enzyme, heat denaturation of nucleic acid, or reverse transcription of the RNA into cDNA. Similarly, metal chelating compounds may inhibit one or more of these analysis steps.

The present inventors have discovered that phosphorous or sulfur containing compounds (e.g., wherein the phosphorous or sulfur is in the form of phosphate or sulfate) can surprisingly increase the stability of RNA in solution at temperatures above, or above about, 4° C., 6° C., or 8° C. Accordingly, described herein are methods, compositions, and reaction mixtures for increasing the stability of RNA in solution with a phosphorous or a sulfur-containing compound. Such methods, compositions, and reaction mixtures can be used, e.g., to reduce or eliminate RNA degradation (e.g., metal catalyzed, autocatalytic, enzymatic, or otherwise) before, during, or after one or more RNA preparation, storage, manipulation, or analysis steps. For example, methods, compositions, and reaction mixtures are described herein for improving RNA stability before, during, or after in vitro transcription, RNA amplification, in vitro translation, DNase digestion, heat inactivation of DNase, or incubation of the RNA in solution at an elevated temperature (e.g., at a temperature of about, or at least about, 10° C., 15° C., 20° C., 25° C., 37° C., 40° C., 50° C., 55° C., 58° C., 60° C., 65° C., 70° C., or 75° C.). In some cases, the methods compositions, and reaction mixtures can improve RNA stability in a solution at an elevated temperature of less than about 110° C., 104° C., 100° C., 99° C., 98° C., 97° C., 96° C., 95° C., 90° C., 85° C., or 80° C.

In some cases, the methods compositions, and reaction mixtures can improve RNA stability in a solution at a temperature of between about 10° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., 30° C., 25° C. or 20° C.; between about 15° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., 30° C., 25° C. or 20° C.; between about 20° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., 30° C., or 25° C.; or between about 25° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., or 30° C.

In some cases, the methods compositions, and reaction mixtures can improve RNA stability in a solution at a temperature of between about 25° C. and about 110° C., between about 25° C. and about 100° C., between about 25° C. and about 99° C., between about 25° C. and about 95° C., between about 25° C. and about 90° C., between about 25° C. and about 85° C., between about 25° C. and about 80° C., between about 25° C. and about 75° C., between about 25° C. and about 70° C., between about 25° C. and about 65° C., between about 25° C. and about 60° C., between about 25° C. and about 55° C., between about 30° C. and about 110° C., between about 30° C. and about 100° C., between about 30° C. and about 95° C., between about 30° C. and about 90° C., between about 30° C. and about 85° C., between about 30° C. and about 80° C., between about 30° C. and about 75° C., between about 30° C. and about 70° C., between about 30° C. and about 65° C., between about 40° C. and about 110° C., between about 40° C. and about 100° C., between about 40° C. and about 95° C., between about 40° C. and about 90° C., between about 40° C. and about 85° C., between about 40° C. and about 80° C., between about 40° C. and about 75° C., between about 40° C. and about 70° C., or between about 40° C. and about 65° C.

II. Methods

Described herein are methods for protecting RNA from degradation in solution. In some embodiments, the method comprises forming or providing a solution (e.g., a reaction mixture) containing water, RNA, divalent cations, and a phosphorous or sulfur-containing compound; and, incubating the solution at a temperature of at least 10° C., 15° C., 20° C., 25° C., 30° C., 35° C., 37° C., 40° C., 50° C., 55° C., 60° C., 65° C., 70° C., or 75° C., wherein the RNA is protected from degradation as compared to an RNA in an aqueous solution that contains the divalent cations but does not contain the phosphorous-containing or sulfur-containing compound.

In some cases, the method includes incubating the solution at a temperature of less than, or less than about, 110° C., 104° C., 100° C., 99° C., 98° C., 97° C., 96° C., 95° C., 90° C., 85° C., or 80° C. In some cases, the method includes incubating the solution at a temperature of, of about, of at least, or of at least about 37° C., 38° C., 40° C., 42° C., 45° C., 50° C., 55° C., 60° C., 65° C., 70° C., or 75° C. In some cases, the method includes incubating the solution at a temperature of, of about, of at least, or of at least about 50° C., 55° C., 60° C., 65° C., 70° C., or 75° C. In some cases, the method includes incubating the solution at a temperature of, of about, of at least, or of at least about 55° C., 56° C., 60° C., 65° C., 70° C., or 75° C.

In some cases, the method includes incubating the solution at a temperature of between about 10° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., 30° C., 25° C. or 20° C.; between about 15° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., 30° C., 25° C. or 20° C.; between about 20° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., 30° C., or 25° C.; or between about 25° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., or 30° C. In some cases, the method includes incubating the solution at a temperature of between about 25° C. and about 110° C., between about 25° C. and about 100° C., between about 25° C. and about 99° C., between about 25° C. and about 95° C., between about 25° C. and about 90° C., between about 25° C. and about 85° C., between about 25° C. and about 80° C., between about 25° C. and about 75° C., between about 25° C. and about 70° C., between about 25° C. and about 65° C., between about 25° C. and about 60° C., between about 25° C. and about 55° C., between about 30° C. and about 110° C., between about 30° C. and about 100° C., between about 30° C. and about 95° C., between about 30° C. and about 90° C., between about 30° C. and about 85° C., between about 30° C. and about 80° C., between about 30° C. and about 75° C., between about 30° C. and about 70° C., between about 30° C. and about 65° C., between about 40° C. and about 110° C., between about 40° C. and about 100° C., between about 40° C. and about 95° C., between about 40° C. and about 90° C., between about 40° C. and about 85° C., between about 40° C. and about 80° C., between about 40° C. and about 75° C., between about 40° C. and about 70° C., or between about 40° C. and about 65° C.

In some cases, the incubating at one or more of the foregoing temperatures or temperature ranges comprises heat inactivating a (e.g., recombinant and/or heterologous) DNase enzyme. Suitable incubation temperatures and times for DNase enzyme heat inactivation are described herein. For example, heat inactivating DNase enzyme can, e.g., be performed a duration of, of about, of at least, or of at least about, 5 s, 10 s, 15 s, 30 s, 1 min, 2 min, 3 min, 4 min, 5 min, 7.5 min, 10 min, 15 min, 20 min, 30 min, 45 min, or 1 hr. In some cases, heat inactivating DNase enzyme is performed for between about 5 min and 30 min, between about 7 min and 20 min, or about 10 min. In an exemplary embodiment, DNase is heat inactivated at about 75° C. for about 10 minutes, at about 75° C. for about 10 minutes, or at about 70° C. for about 25-30 minutes. In some cases, the DNase is a heat-labile DNase and is heat inactivated by incubating the solution at a temperature of about 58° C. for about 5 minutes. Further incubation times and temperatures are described below.

For example, the RNA can be protected from degradation by the presence of the phosphorous or sulfur containing compound as compared to degradation obtained by incubating RNA in an otherwise identical, or substantially identical, solution. For instance, the RNA can be protected from degradation as compared to a solution of the same or similar divalent cation concentration, pH, or temperature.

In some cases, the incubating at one or more of the foregoing temperatures or temperature ranges comprises storing the RNA solution. For example, the RNA solution can be stored at about at temperatures above, or above about, 4° C., 6° C., 8° C., or 10° C. In some cases, the RNA solution can be stored at a temperature between about 4° C. and about 37° C., between about 10° C. and about 37° C., between about 15° C. and about 37° C., between about 4° C. and about 30° C., between about 10° C. and about 30° C., between about 15° C. and about 30° C., between about 4° C. and about 25° C., or between about 10° C. and about 25° C. In some cases, the RNA stabilized RNA solution can be stored for at least about 4 hrs, 8 hrs, 12 hrs, 16 hrs, 18 hrs, 20 hrs, 24 hrs, 1.5 days, 2 days, 3 days, or more.

In some cases, the RNA can be protected from autocatalytic degradation. For example, the RNA can be protected from alkali-promoted transesterification-mediated autocatalytic degradation. See, e.g., J. Am. Chem. Soc., 1999, 121, 5364-72. In some cases, the phosphorous or sulfur containing compound can inhibit autocatalytic degradation by interacting with the hydroxyl group at the 2' position of one or more ribose sugars of the RNA backbone. In some cases, this interaction can reduce, inhibit, or block, nucleophilic attack of one or more phosphodiester bonds of the RNA by the oxygen of the 2' hydroxyl group.

In some cases, the reaction mixture contains RNA purified from an organism, cell, or tissue. Methods, compositions, and kits for purification of RNA from organisms, cells, or tissues include, but are not limited to those using or containing guanidinium thiocynate and phenol. See, Chomczynski & Sacchi, Anal Biochem. 1987 April; 162(1):156-9. Additionally, or alternatively, the RNA can be purified from an organism, cell, or tissue by alcohol precipitation, or solid phase purification techniques (e.g., oligodT beads, columns, and the like).

In some embodiments, the RNA is free, or substantially free, of endogenous host proteins from the cell or tissue from which the RNA has been purified. For example, in some cases the provided solution containing RNA is not a purified preparation of protein or protein:RNA complex from the host cell, organism, or tissue. As another example, the provided solution containing RNA is not a cell lysate or a subcellular fraction thereof (e.g., a cytosolic, nuclear, or nucleolus fraction). As yet another example, the provided solution containing RNA is not conditioned media.

The provided solution containing RNA can contain RNA at a wide range of suitable concentrations. For example, the RNA can be a stock solution of RNA at a high concentration, which stock can be diluted for one or more subsequent analytical or preparatory methods. Thus, the RNA can be at a concentration of 500 μg/mL, or 1 mg/mL, or more. In some cases, the RNA is at a concentration of from 0.1 pg/mL to 500 μg/mL. In some cases, the RNA is at a concentration suitable for performing a DNase reaction to remove contaminating genomic DNA. In some cases, the RNA is at a concentration suitable for performing a reverse transcription reaction to form cDNA from the RNA template or a portion thereof. In some cases, the RNA can be at a concentration of between about 10 pg/mL to about 100 µg/mL; between about 50 pg/mL to about 100 µg/mL; between about 60 pg/mL to about 60 µg/mL; or at a concentration of about 50 pg/mL; 60 pg/mL; 70 pg/mL; 80 pg/mL; 90 pg/mL; 100 pg/mL; 1 µg/mL; 5 µg/mL; 10 µg/mL; 25 µg/mL; 50 µg/mL; 75 µg/mL; 100 µg/mL; 150 µg/mL; 200 µg/mL; 250 µg/mL; 300 µg/mL; 400 µg/mL; 500 µg/mL; or more.

In some embodiments, the provided solution containing RNA also contains DNA, for example genomic DNA. In some cases, the DNA is derived from, extracted from, or purified from, the same cell, organism, or tissue that is the origin of the RNA. In some cases, the DNA is double stranded DNA, or double stranded or single-stranded genomic DNA. In some cases, the DNA is DNase digested. In some cases, the RNA and DNA, or portions thereof, are in an RNA DNA hybrid.

In some cases the DNA is at a concentration that is less than the RNA in the solution. For example, the DNA can be at a concentration that is 30%, 10% of, 1% of, or less than 30%, 10%, or 1% of, the concentration of the RNA in the solution. In some cases, the mass of the DNA in the solution is 30%, 10%, 5%, 1%, or less than 1% of the mass of the RNA in the solution. In some cases, the ratio of the mass of the DNA to the mass of the RNA in the solution can be about, or be less than about, 1/3, 1/4, 1/5, 1/6, 1/10, 1/15, 1/20, 1/25, 1/30, 1/50, 1/100, 1/200, 1/250, 1/300, 1/400, 1/500, or 1/1000. In some cases, the DNA in the provided solution containing RNA is at a concentration of about, or at a concentration of less than about, 1 mg/mL, 500 µg/mL, 250 µg/mL, 100 µg/mL, 50 µg/mL, 40 µg/mL, 30 µg/mL, 25 µg/mL, 20 µg/mL, 15 µg/mL, 10 µg/mL, 5 µg/mL, 1 µg/mL, 500 ng/mL, 250 ng/mL, 100 ng/mL, 50 ng/mL, 25 ng/mL, 20 ng/mL, 15 ng/mL, 10 ng/mL, 5 ng/mL, or 1 ng/mL. As such, the DNA in the provided solution containing RNA can be at a concentration of about, or at a concentration of less than about, 1 µg/µL, 500 ng/µL, 250 ng/µL, 100 ng/µL, 50 ng/µL, 40 ng/µL, 30 ng/µL, 25 ng/µL, 20 ng/µL, 15 ng/µL, 10 ng/µL, 5 ng/µL, 1 ng/µL, 500 pg/µL, 250 pg/µL, 100 pg/µL, 50 pg/µL, 25 pg/µL, 20 pg/µL, 15 pg/µL, 10 pg/µL, 5 pg/µL, or 1 pg/µL. In some cases, the DNA in the provided solution containing RNA is at a concentration of about, or at a concentration of less than about, 1 ng/mL, 500 pg/mL, 250 pg/mL, 100 pg/mL, 50 pg/mL, 25 pg/mL, 20 pg/mL, 15 pg/mL, 10 pg/mL, 5 pg/mL, or 1 pg/mL.

In one embodiment, the provided solution containing RNA is a solution containing purified RNA in a digestion buffer suitable for digestion of contaminating DNA or genomic DNA (if present) by a DNase enzyme. For example, the solution can contain DNase enzyme. As another example, the solution can contain calcium or magnesium ions necessary for enzymatic degradation of the DNA by DNase. In some cases, the DNase enzyme is not a DNase enzyme endogenous to a host organism, cell, or tissue from which the RNA is extracted or otherwise derived. In some cases, the DNase enzyme is exogenous or heterologous to a host organism, cell, or tissue from which the RNA is extracted or otherwise derived. In some cases, the DNase enzyme is a recombinant enzyme. Suitable recombinant enzymes include recombinant bovine pancreas DNase I (e.g., available from New England Biolabs). Other suitable recombinant enzymes can include enzymes that are naturally, or have been modified to be, more heat-labile than bovine pancreas DNase I, such as for example, HL-dsDNase, available from ArcticZymes.

In some cases, the provided solution contains DNase enzyme at a concentration of from about 0.01 U/µL to about 0.2 U/µL; or from about 0.019 to about 0.125 U/µL. In some cases, the provided solution contains DNase enzyme at a concentration of, of about, or at least about 0.01, 0.02, 0.03, 0.04, 0.05, 0.06, 0.0625, 0.07, 0.08, 0.09, 0.1, 0.125, 0.15, 0.175, or 0.2 U/µL. In some cases, the DNase enzyme is heat inactivated, and the concentration in units per volume refers to the corresponding concentration in units per volume for a DNase that has not been heat inactivated.

In some embodiments, the provided solution is incubated at a temperature, and under conditions, suitable for performing a DNase reaction. The DNase reaction can be performed prior to a higher or lower temperature incubation. For example, the DNase reaction can be performed prior to heat inactivating the DNase. As another example, the DNase reaction can be performed, and then the reaction mixture cooled to a low temperature (e.g., 4° C.) for storage. As yet another example, the DNase reaction can be performed, the reaction mixture optionally cooled, and then the reaction mixture, or a portion thereof, can be heated to inactivate DNase, perform a reverse transcription reaction using the RNA as a template, or amplify the RNA or cDNA derived therefrom, or a combination thereof.

Suitable temperatures for performing a DNase reaction can depend on the type of DNase enzyme in the reaction mixture. For example, a suitable temperature for a DNase reaction with a DNase enzyme from a thermophile or hyperthermophile can be higher than a suitable temperature for a DNase enzyme from a mesophile. In some embodiments, suitable temperatures for performing a DNase reaction can include, but are not limited to a temperature of about 20° C., 25° C., 30° C., 31° C., 32° C., 33° C., 34° C., 35° C., 36° C. 37° C., 38° C., 39° C., 40° C., 41° C., 42° C., 43° C., 44° C., or 45° C.

Suitable temperatures for inactivating DNase can depend on the type of DNase enzyme in the reaction mixture. For example, cold-adapted or heat-labile DNase enzymes can be inactivated at lower temperatures than mesophilic or thermophilic DNase enzymes. In some cases, the DNase enzyme is a heat-labile DNase enzyme and can be inactivated at a temperature of about, or at least about, 40° C., 45° C., 50° C., 51° C., 52° C., 53° C., 54° C., 55° C., 56° C., 57° C., 58° C., 59° C., or 60° C. In some cases, the DNase enzyme is from a mesophilic organism (e.g., such as bone pancreas DNase I) and can be heat inactivated at a temperature of about, or at least about, 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C. or 80° C. In some cases, the heat-labile or mesophilic DNase enzyme is heat inactivated at a temperature of less than about 110° C., 104° C., 100° C., 99° C., 98° C., 97° C., 96° C., 95° C., 90° C., 85° C., or 80° C.

Heat inactivation of DNase can be performed by incubating the solution containing RNA for a sufficient time at the heat inactivation temperature. In some cases, a higher temperature can achieve heat inactivation in a shorter period of time. In some cases, a longer period of high temperature incubation can be required if the heat inactivation temperature is relatively low. Suitable heat inactivation times include, but are not limited to, about or at least about 0.5 minutes, 1 minute, 5 minutes, 10 minutes, 15 minutes, or 30 minutes.

In some embodiments, the method comprises reverse transcribing the RNA, or a specific region, molecule, or sequence of the RNA into cDNA. The reverse transcription reaction can be performed by a variety of methods. For example, the RNA can be contacted with a reverse transcriptase enzyme, and a specific primer that hybridizes to a specific region, molecule, or sequence of the RNA. As another example, the RNA can be contacted with an oligodT oligonucleotide and a reverse transcriptase to reverse transcribe polyadenylated RNA. As yet another example, the RNA can be contacted with a set of degenerate primers (e.g., random hexamers, septamers, octomers, nonomers, decamers, or a combination thereof) and a reverse transcriptase to reverse transcribe total RNA. As yet another example, the RNA can be contacted with a combination of oligodT and degenerate primers and a reverse transcriptase.

In some embodiments, after the step of reverse transcribing the RNA, the RNA template is degraded. In some cases, after the step of reverse transcribing the RNA, RNA that is in an RNA/DNA hybrid is degraded. In some cases, the RNA template can be contacted with an RNase H enzyme to degrade RNA in an RNA/DNA hybrid. In some cases, the degradation of the RNA in an RNA:DNA hybrid produced during first strand synthesis of the cDNA by reverse transcriptase is then followed by second strand synthesis of the cDNA. In some cases, the provided solution containing RNA is RNase free prior to contact with a reverse transcriptase. In some cases, the provided solution containing RNA is RNase free prior to contact with an RNase H, or prior to degradation by RNase H of an RNA:DNA hybrid generated by contacting a reverse transcriptase with the RNA template.

In some embodiments, the method comprises quantifying the amount of RNA in the solution, or quantifying the amount of a specific region or sequence of RNA in the solution. In some cases, the quantifying of RNA is performed after a step of removing or digesting DNA in the solution. In some cases, the quantifying of RNA is performed after a step of DNase digestion. In some cases, the quantifying of RNA is performed after a step of DNase digestion and heat inactivation of the DNase. In some cases, the quantification is performed after a step of incubating the provided solution containing RNA at a temperature of at least 37° C., 40° C., 50° C., 55° C., 60° C., 65° C., 70° C., or 75° C., wherein the RNA is protected from degradation at this incubation temperature as compared to an RNA in an aqueous solution that contains the divalent cations but does not contain the phosphorous-containing or sulfur-containing compound. In some cases, the temperature of the solution is less than about 110° C., 104° C., 100° C., 99° C., 98° C., 97° C., 96° C., 95° C., 90° C., 85° C., or 80° C.

In some cases, this protection of the RNA from degradation provides a greater accuracy of quantitation as compared to quantitation of RNA in an aqueous solution that contains the divalent cations but does not contain the phosphorous-containing or sulfur-containing compound. In some cases, the accuracy of quantitation is an accuracy of the amount of RNA in the solution prior to an incubation at a temperature of at least 10° C., 15° C., 20° C., 25° C., 30° C., 37° C., 40° C., 50° C., 55° C., 60° C., 65° C., 70° C., or 75° C. For example, the degraded RNA can result in the detection of an erroneously low quantity of RNA as compared to the amount of RNA prior to the incubation at a temperature of at least 10° C., 15° C., 20° C., 25° C., 30° C., 37° C., 40° C., 50° C., 55° C., 60° C., 65° C., 70° C., or 75° C., or prior to a DNase digestion or heat inactivation of DNase.

The RNA can be quantified by a variety of methods known in the art. For example, the RNA can be contacted with a dye that detectably labels the RNA. In some cases, unbound dye can be separated from RNA-bound dye. The quantity of RNA-bound dye can then be analyzed, e.g., by spectroscopic or fluorometric techniques, to quantify the amount of RNA. Alternatively, e.g., if the dye provides a detectably distinguishable signal (e.g., an increase in fluorescence) when bound to RNA as compared to a signal in the unbound state, a separation step may not be required.

In some embodiments, the RNA quantification includes a step of reverse transcribing the RNA. For example, the RNA can be reverse transcribed into cDNA, and the amount of resulting cDNA detected. In some cases, the amount of cDNA is detected by use of an intercalating nucleic acid dye. In some cases, the amount of cDNA is detected by amplifying at least a portion of the cDNA using a DNA-dependent DNA polymerase and one or more primers, and monitoring the amplification reaction. Methods for reverse transcribing RNA and quantitating the amount of resulting cDNA by monitoring the amplification reaction are generally referred to as RT-qPCR assays. Methods for performing RT-qPCR assays are generally known in the art.

In some cases, the RT-qPCR is performed using a non-specific amplicon detection reagent. For example, an intercalating dye that recognizes double stranded DNA amplicons can be used to monitor amplification. Alternatively, the RT-qPCR can be performed using a specific amplicon detection reagent. Examples of specific amplicon detection reagents include nucleic acid probes, such as scorpion probes, Taq-man probes, and molecular beacons. Further examples include locked nucleic acid probes, peptide nucleic acid probes, aptamers, and the like.

In some embodiments, the RNA quantification includes a step of hybridizing the RNA, or cDNA reverse-transcribed derived therefrom, to an immobilized complementary nucleic acid. For example, the RNA, or cDNA reverse-transcribed therefrom, can be hybridized to a microarray, flow cell, or other solid surface containing one or more complementary immobilized capture oligonucleotides. In some cases, the RNA quantification includes a step of sequencing the RNA, or cDNA reverse-transcribed derived therefrom.

The provided RNA solution contains a phosphorous or sulfur containing compound. In some cases, the phosphorous containing compound is a phosphine. In some cases, the phosphorous containing compound is a compound containing a phosphorous atom with a direct covalent bond to one, two, three, or four oxygen atoms. In some cases, the phosphorous containing compound is a phosphorus oxide. In some cases, the phosphorous containing compound is a phosphorus oxyacid (i.e., a phosphorous compound containing at least one hydroxyl group covalently bonded to the phosphorous atom). In some cases, the phosphorous containing compound is a phosphite, or phosphonate, or an organophosphate. In some cases, the organophosphate is a glycerol phosphate, such as β-glycerol phosphate (glycerol 3-phosphate), a ribose phosphate, a glucose phosphate, or a fructose phosphate. In some cases, the phosphorous containing compound is a phosphodiester. In the context of the present disclosure, the phosphorous containing compound is not a DNA or RNA oligonucleotide. In some cases, the phosphorous-containing compound is heterologous to the RNA in the solution.

In an exemplary embodiment, the phosphorous containing compound is a phosphate. In this embodiment, the provided solution containing RNA and phosphate can, e.g., be provided by introducing into a solution a variety of different phosphate salts. For example, the phosphate can be provided into the solution as a dibasic, monobasic, or tribasic sodium or potassium phosphate salt.

In some cases, the phosphorous containing compound is a pyrophosphate, diphosphate, or triphosphate containing compound. For example, the phosphorus containing compound can be pyrophosphate, diphosphate, triphosphate, or a derivative thereof. Exemplary derivatives of pyrophosphate include, but are not limited to nucleoside pyrophosphates such as adenosine, inosine, uracil, guanine, thymine, or cytosine pyrophosphate. Exemplary derivatives of triphosphate include, but are not limited to nucleoside triphosphates such as adenosine, inosine, uracil, guanine, thymine, or cytosine triphosphate. In some cases, the phosphorous containing compound is a higher order polyphosphate, such as a species of the formula $[NaPO_3]_n[NaPO_3(OH)]_2$, $[KPO_3]_n[KPO_3(OH)]_2$, $[NaPO_3]_n[KPO_3(OH)]_2$, or $[KPO_3]_n[NaPO_3(OH)]_2$, wherein n is from 2 or 3 to 2000 or more.

In an exemplary embodiment, the sulfur containing compound is a sulfate. In this embodiment, the provided solution containing RNA and sulfate can, e.g., be provided by introducing into a solution a variety of different sulfate salts. For example, the sulfate can be provided into the solution as sodium sulfate, magnesium sulfate, ammonium sulfate, or a combination thereof. In some cases, the sulfur-containing compound is heterologous to the RNA in the solution.

In some cases, pH of the provided solution containing RNA and a phosphorous or sulfur containing compound can be adjusted or configured to maintain a certain pH or pH range. For example, in some cases, the phosphorous or sulfur containing compound can be a strong or weak acid, a strong or weak base, or act as a pH buffering agent. The phosphorous or sulfur containing compound can thus alter the pH of the solution. In some cases, this pH alteration is mitigated by including an additional buffering agent into the provided solution containing RNA.

Exemplary buffering agents include, but are not limited to, one or more of the following: tris(hydroxymethyl)aminomethane (TRIS), N-2-hydroxyethylpiperazine-N'-2-aminoethane sulfonic acid (HEPES), N-tris-(hydroxymethyl)methyl-2-aminoethane sulfonic acid (TES), N-tris (hydroxymethyl) methylglycine (Tricene), 2-(N-morpholino)ethane sulfonic acid (IVIES), bis-(2-hydroxyethyl)imino-tris-(hydroxymethyl)methane (bis-tris), N-2-acetamidoiminodiacetic acid (ADA), N-(2-acetamido) iminodiacetic acid (ACES), piperazine-N,N'-bis(2-ethanesulfonic acid) (PIPS), 3-(N-morpholine)-2-hydroxypropane sulfonic acid (MOPSO), 1,3-bis[tris(hydroxymethyl)methylamino]propane(bis-tris propane), N,N-bis-(2-hydroxyethyl)-2-aminoethane sulfonic acid (BES), 3-(N-morpholine)propane sulfonic acid (MOPS), 3-[N-bis(hydroxyethyl)-amino]-2-hydroxypropane sulfonic acid (DIPSO), 3-[N-(tris-hydroxymethyl)methylamino]-2-hydroxypropane sulfonic acid (TAPSO), piperazine-N,N'bis-(2-hydroxypropane) sulfonic acid (POPSO), N-hydroxyethylpiperazine-N'-2-hydroxypropane sulfonic acid (HEPPSO), N-2-hydroxyethylpiperazine-N'-2-aminopropane sulfonic acid (EPPS), N,N-bis-(2-hydroxyethyl)glycine (bicine), N-tris(hydroxymethyl)methyl-3-aminopropane sulfonic acid (TAPS), 3-N-(α,α-dimethylhydroxuethyl)-amino-2-hydroxypropane sulfonic acid (AMPSO) and 3-N-cyclohexylamino sulfonic acid (CAPSO).

In some cases, the pH of the provided solution containing RNA is adjusted or maintained to be between about 6 to about 8.5. In some cases, the pH of the provided solution containing RNA is adjusted or maintained to be between about 6.5 to about 8. In some cases, the pH of the provided solution containing RNA is adjusted or maintained to be between about 7 to about 8. In some cases, the pH of the provided solution containing RNA is adjusted or maintained to be, or be about, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or 8.5. In some cases, the pH of the provided solution containing RNA is adjusted or maintained to be a pH that eliminates or minimizes precipitation of phosphate ions, calcium ions, or calcium phosphate, if present.

In some embodiments, the phosphorous-containing or sulfur-containing compound is at a concentration of from about 0.1 mM to about 500 mM. In some embodiments, the phosphorous-containing or sulfur-containing compound is at a concentration of from about 0.5 mM to about 250 mM. In some embodiments, the phosphorous-containing or sulfur-containing compound is at a concentration of from about 0.5 mM to about 100 mM. In some embodiments, the phosphorous-containing or sulfur-containing compound is at a concentration of from about 0.5 mM to about 50 mM. In some embodiments, the phosphorous-containing or sulfur-containing compound is at a concentration of from about 0.5 mM to about 25 mM. In some embodiments, the phosphorous-containing or sulfur-containing compound is at a concentration of from about 0.5 mM to about 15 mM. In some embodiments, the phosphorous-containing or sulfur-containing compound is at a concentration of about, or of at least about, 0.1 mM, 0.2 mM, 0.3 mM, 0.4 mM, 0.5 mM, 0.6 mM, 0.7 mM, 0.8 mM, 0.9 mM, 1 mM, 1.5 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, or 22 mM, 23 mM, 24 mM, or 25 mM.

In some embodiments, the phosphorous-containing or sulfur-containing compound is sodium or potassium phosphate (monobasic, dibasic, or tribasic) at a concentration of 0.1 mM, 0.2 mM, 0.3 mM, 0.4 mM, 0.5 mM, 0.6 mM, 0.7 mM, 0.8 mM, 0.9 mM, 1 mM, 1.5 mM, 2 mM, 3 mM, 4 mM, 5 mM, 6 mM, 7 mM, 8 mM, 9 mM, 10 mM, 11 mM, 12 mM, 13 mM, 14 mM, or 15 mM. In some embodiments, the phosphorous-containing or sulfur-containing compound is provided as a sulfate salt (e.g., sodium sulfate, magnesium sulfate, ammonium sulfate) at a concentration of 1 mM, 1.5 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, or 22 mM, 23 mM, 24 mM, or 25 mM. In some embodiments, the phosphorous-containing or sulfur-containing compound is β-glycerol phosphate at a concentration of 1 mM, 1.5 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, or 22 mM, 23 mM, 24 mM, or 25 mM.

The provided RNA solution contains divalent cations. In some cases, the divalent cations are divalent magnesium cations. In some cases, the divalent cations are calcium divalent cations. In some cases, the divalent cations are manganese divalent cations. In some cases the divalent cations can be a required component of the solution for carrying out one or more enzymatic reactions, including, but not limited to DNase digestion, reverse transcription, degradation of RNA in an RNA:DNA hybrid, second strand cDNA synthesis, or nucleic acid amplification. In some cases, the provided solution contains two or more different divalent cations, such as magnesium and calcium divalent cations.

In some embodiments, the provided RNA solution contains divalent calcium cations at a concentration of from about 10 µM to about 100 mM. In some embodiments, the provided RNA solution contains divalent calcium cations at a concentration of from about 10 µM to about 50 mM. In some embodiments, the provided RNA solution contains divalent calcium cations at a concentration of from about 10 µM to about 10 mM. In some embodiments, the provided RNA solution contains divalent calcium cations at a concentration of from about 100 µM to about 10 mM. In some embodiments, the provided RNA solution contains divalent calcium cations at a concentration of from about 250 µM to about 10 mM. In some embodiments, the provided RNA solution contains divalent calcium cations at a concentration of from about 250 µM to about 5 mM. In some embodiments, the provided RNA solution contains divalent calcium cations at a concentration of from about 0.5 mM to about 5 mM. In some embodiments, the provided RNA solution contains divalent calcium cations at a concentration of, or of about, 0.01 mM, 0.02 mM, 0.03 mM, 0.04 mM, 0.05 mM, 0.075 mM, 0.1 mM, 0.2 mM, 0.3 mM, 0.4 mM, 0.5 mM, 0.6 mM, 0.7 mM, 0.8 mM, 0.9 mM, 1 mM, 1.5 mM, 2 mM, 2.5 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, or 22 mM, 23 mM, 24 mM, or 25 mM.

In some embodiments, the provided RNA solution contains divalent magnesium cations at a concentration of from about 10 µM to about 100 mM. In some embodiments, the provided RNA solution contains divalent magnesium cations at a concentration of from about 10 µM to about 50 mM. In some embodiments, the provided RNA solution contains divalent magnesium cations at a concentration of from about 10 µM to about 10 mM. In some embodiments, the provided RNA solution contains divalent magnesium cations at a concentration of from about 10 µM to about 10 mM. In some embodiments, the provided RNA solution contains divalent magnesium cations at a concentration of from about 100 µM to about 10 mM. In some embodiments, the provided RNA solution contains divalent magnesium cations at a concentration of from about 250 µM to about 10 mM. In some embodiments, the provided RNA solution contains divalent magnesium cations at a concentration of from about 250 µM to about 5 mM. In some embodiments, the provided RNA solution contains divalent magnesium cations at a concentration of from about 0.5 mM to about 5 mM. In some embodiments, the provided RNA solution contains divalent magnesium cations at a concentration of, or of about, 0.01 mM, 0.02 mM, 0.03 mM, 0.04 mM, 0.05 mM, 0.075 mM, 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.5 mM, 2 mM, 2.5 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, or 22 mM, 23 mM, 24 mM, or 25 mM.

In some embodiments, the provided solution containing RNA contains calcium divalent cations at a concentration of from 10 µM to 0.5 mM, 10 µM to 1 mM, 10 µM to 2 mM, 10 µM to 3 mM, 10 µM to 4 mM, or 10 µM to 5 mM and magnesium divalent cations at a concentration of from 0.1 mM to 2.5 mM, 0.1 mM to 5 mM, 0.1 mM to 10 mM, 0.1 mM to 15 mM, 0.1 mM to 20 mM, 0.1 mM to 30 mM, 0.1 mM to 50 mM, 0.01 to 10 mM, 0.01 to 15 mM, 0.01 mM to 20 mM, 0.01 mM to 30 mM, or 0.01 mM to 50 mM. In some cases, the provided solution containing RNA contains calcium divalent cations at a concentration of from 0.1 mM to 1 mM and magnesium divalent cations at a concentration of from 0.5 mM to 5 mM. In some cases, the provided solution containing RNA contains calcium divalent cations at a concentration of about 0.5 mM and magnesium divalent cations at a concentration of about 2.5 mM.

The methods describe herein include a wide array of different parameters (e.g., time, temperature, amount, and concentration), components (e.g., RNA, DNA, DNase, RNase H, reverse transcriptase, DNA-dependent polymerase, phosphorous or sulfur containing compound, primers, probes, and cations), and conditions (e.g., RNase free, free of host cell proteins, exogenous, heterologous, recombinant, digested, and protected from degradation). Such methods include any combination of parameters, components, or conditions described herein.

III. Compositions

Described herein are compositions for protecting RNA from degradation in solution. Compositions described herein can protect the RNA from autocatalytic degradation, metal catalyzed degradation, alkali-promoted transesterification-mediated autocatalytic degradation, and the like. In some cases, the RNA can be protected from degradation in a solution at an elevated temperature (e.g., elevated above 4° C.). In some cases, the RNA can be protected from degradation in solution by the presence of the phosphorous or sulfur containing compound as compared to degradation obtained by incubating RNA in an otherwise identical, or substantially identical, solution. For instance, the RNA can be protected from degradation as compared to a solution of the same or similar divalent cation concentration, pH, or temperature.

Described herein is a solution containing water, RNA, divalent cations, and a phosphorous or sulfur containing compound, wherein the RNA is protected from degradation as compared to an RNA in an aqueous solution that contains the divalent cations but does not contain the phosphorous-containing or sulfur-containing compound. In some cases, the RNA is protected from degradation at a temperature of at least 10° C., 15° C., 20° C., 25° C., 30° C., 35° C., 37° C., 40° C., 50° C., 55° C., 60° C., 65° C., 70° C., or 75° C. as compared to RNA in an otherwise identical solution that does not contain a phosphorous or sulfur containing compound.

In some cases, the RNA is protected from degradation at a temperature between about 10° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., 30° C., 25° C. or 20° C.; between about 15° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., 30° C., 25° C. or 20° C.; between about 20° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., 30° C., or 25° C.; or between about 25° C. and about 110° C., 104° C., 100° C., 99° C., 98° C., 97° C., 96° C., 95° C., 90° C., 85° C., 80° C., 75° C., 70° C., 65° C., 60° C., 55° C., 50° C., 45° C., 40° C., 37° C., 35° C., or 30° C.

In some cases, the RNA is protected from degradation at a temperature between about 25° C. and about 110° C., between about 25° C. and about 100° C., between about 25° C. and about 99° C., between about 25° C. and about 95° C., between about 25° C. and about 90° C., between about 25° C. and about 85° C., between about 25° C. and about 80° C., between about 25° C. and about 75° C., between about 25° C. and about 70° C., between about 25° C. and about 65° C., between about 25° C. and about 60° C., between about 25°

C. and about 55° C., between about 30° C. and about 110° C., between about 30° C. and about 100° C., between about 30° C. and about 95° C., between about 30° C. and about 90° C., between about 30° C. and about 85° C., between about 30° C. and about 80° C., between about 30° C. and about 75° C., between about 30° C. and about 70° C., between about 30° C. and about 65° C., between about 40° C. and about 110° C., between about 40° C. and about 100° C., between about 40° C. and about 95° C., between about 40° C. and about 90° C., between about 40° C. and about 85° C., between about 40° C. and about 80° C., between about 40° C. and about 75° C., between about 40° C. and about 70° C., or between about 40° C. and about 65° C.

In some cases, the solution containing water, divalent cations, and a phosphorous or sulfur containing compound is configured to provide a more accurate quantitation of a concentration of the RNA in the solution as compared to an RNA in an aqueous solution that contains the divalent cations but does not contain the phosphorous-containing or sulfur-containing compound. In some cases, the accuracy of quantitation is an accuracy of the amount of RNA in the solution prior to an incubation at a temperature of at least 10° C., 15° C., 20° C., 25° C., 30° C., 37° C., 40° C., 50° C., 55° C., 60° C., 65° C., 70° C., or 75° C. For example, the degraded RNA can result in the detection of an erroneously low quantity of RNA as compared to the amount of RNA prior to the incubation at a temperature of at least 10° C., 15° C., 20° C., 25° C., 30° C., 37° C., 40° C., 50° C., 55° C., 60° C., 65° C., 70° C., or 75° C., or prior to a DNase digestion or heat inactivation of DNase.

In some cases, the solution is compatible with reverse transcription of the RNA into cDNA. A compatible solution can contain reverse transcriptase enzyme and the template RNA. A compatible solution can further contain dNTPs and one or more oligonucleotide primers. A compatible solution can further contain divalent magnesium ions. A compatible solution can further contain a buffering agent, one or more potassium or sodium chloride or sulfate salts, and optionally a reducing agent. In one embodiment, the solution contains 25 mM Tris-HCl (pH 8.3), 37.5 mM KCl, 1.5 mM $MgCl_2$. In one embodiment, the solution contains 50 mM Tris-HCl, 75 mM KCl, and 3 mM $MgCl_2$, at a pH of 8.3. In some cases, the solution contains 10 mM DTT or other suitable reducing agent. In some cases, the solution contains actinomycin D. Other suitable conditions compatible for reverse transcription are known in the art.

The solution containing RNA can contain RNA at a wide range of suitable concentrations. For example, the RNA can be a stock solution of RNA at a high concentration, which stock can be diluted for one or more subsequent analytical or preparatory methods. Thus, the RNA can be at a concentration of 500 µg/mL, or 1 mg/mL, or more. In some cases, the RNA is at a concentration of from 0.1 pg/mL to 500 µg/mL. In some cases, the RNA is at a concentration suitable for performing a DNase reaction to remove contaminating genomic DNA. In some cases, the RNA is at a concentration suitable for performing a reverse transcription reaction to form cDNA from the RNA template. In some cases, the RNA can be at a concentration of between about 10 pg/mL to about 100 µg/mL; between about 50 pg/mL to about 100 µg/mL; between about 60 pg/mL to about 60 µg/mL; or at a concentration of about 50 pg/mL; 60 pg/mL; 70 pg/mL; 80 pg/mL; 90 pg/mL; 100 pg/mL; 1 µg/mL; 5 µg/mL; 10 µg/mL; 25 µg/mL; 50 µg/mL; 75 µg/mL; 100 µg/mL; 150 µg/mL; 200 µg/mL; 250 µg/mL; 300 µg/mL; 400 µg/mL; 500 µg/mL; or more.

In some cases, the reaction mixture contains RNA purified from an organism, cell, or tissue. Methods, compositions, and kits for purification of RNA from organisms, cells, or tissues include, but are not limited to those using or containing guanidinium thiocynate and phenol. See, Chomczynski & Sacchi, Anal Biochem. 1987 April; 162(1):156-9. Additionally, or alternatively, the RNA can be purified from an organism, cell, or tissue by alcohol precipitation, or solid phase purification techniques (e.g., oligodT beads, columns, and the like).

In some embodiments, the RNA is free, or substantially free, of endogenous host proteins from the cell or tissue from which the RNA has been purified. For example, in some cases the provided solution containing RNA is not a purified preparation of protein from the host cell, organism, or tissue. As another example, the provided solution containing RNA is not a cell lysate or a subcellular fraction thereof (e.g., a cytosolic, nuclear, or nucleolus fraction). As yet another example, the provided solution containing RNA is not conditioned media.

In some embodiments, the solution containing RNA also contains DNA, for example genomic DNA. In some cases, the DNA is derived from, extracted from, or purified from, the same cell, organism, or tissue that is the origin of the RNA. In some cases, the DNA is double stranded DNA, or double stranded or single-stranded genomic DNA. In some cases, the DNA is DNase digested. In some cases, the RNA and DNA, or portions thereof, are in an RNA DNA hybrid.

In some cases the DNA is at a concentration that is less than the RNA in the solution. For example, the DNA can be at a concentration that is 30%, 10% of, 1% of, or less than 30%, 10%, or 1% of, the concentration of the RNA in the solution. In some cases, the mass of the DNA in the solution is 30%, 10%, 5%, 1% or less than the mass of the RNA in the solution. In some cases, the ratio of the mass of the DNA to the mass of the RNA in the solution can be about, or be less than about, $\frac{1}{3}$, $\frac{1}{4}$, $\frac{1}{5}$, $\frac{1}{6}$, $\frac{1}{10}$, $\frac{1}{15}$, $\frac{1}{20}$, $\frac{1}{25}$, $\frac{1}{30}$, $\frac{1}{50}$, $\frac{1}{100}$, $\frac{1}{200}$, $\frac{1}{250}$, $\frac{1}{300}$, $\frac{1}{400}$, $\frac{1}{500}$, or $\frac{1}{1000}$. In some cases, the DNA in the solution containing RNA is at a concentration of about, or at a concentration of less than about, 1 mg/mL, 500 µg/mL, 250 µg/mL, 100 µg/mL, 50 µg/mL, 40 µg/mL, 30 µg/mL, 25 µg/mL, 20 µg/mL, 15 µg/mL, 10 µg/mL, 5 µg/mL, 1 µg/mL, 500 ng/mL, 250 ng/mL, 100 ng/mL, 50 ng/mL, 25 ng/mL, 20 ng/mL, 15 ng/mL, 10 ng/mL, 5 ng/mL, or 1 ng/mL.

In one embodiment, the solution containing RNA is a solution containing purified RNA in a digestion buffer suitable for digestion of contaminating DNA or genomic DNA (if present) by a DNase enzyme. For example, the solution can contain DNase enzyme. As another example, the solution can contain calcium or magnesium ions necessary for enzymatic degradation of the DNA by DNase. In some cases, the DNase enzyme is not a DNase enzyme endogenous to a host organism, cell, or tissue from which the RNA is extracted or otherwise derived. In some cases, the DNase enzyme is exogenous or heterologous to a host organism, cell, or tissue from which the RNA is extracted or otherwise derived. In some cases, the DNase enzyme is a recombinant enzyme. Suitable recombinant enzymes include recombinant bovine pancreas DNase I (e.g., available from New England Biolabs). Other suitable recombinant enzymes can include enzymes that are naturally, or have been modified to be, more heat-labile than bovine pancreas DNase I, such as for example, HL-dsDNase, available from ArcticZymes.

In some cases, the solution containing RNA contains DNase enzyme at a concentration of from about 0.01 U/µL to about 0.2 U/μL; or from about 0.019 to about 0.125 U/μL. In some cases, the solution contains DNase enzyme at a concentration of, of about, or at least about 0.01, 0.02, 0.03, 0.04, 0.05, 0.06, 0.0625, 0.07, 0.08, 0.09, 0.1, 0.125, 0.15, 0.175, or 0.2 U/μL. In some cases, the DNase enzyme is heat inactivated, and the concentration in units per volume refers to the corresponding concentration in units per volume for a DNase that has not been heat inactivated.

In some cases, the solution is at a temperature of at least, or at least about, 10° C., 15° C., 20° C., 25° C., 30° C., 37° C., 40° C., 42° C., 50° C., 55° C., 58° C., 60° C., 65° C., 70° C., or 75° C. In some cases, the solution is at a temperature of from about 10° C. to at least about 42° C., 50° C., 55° C., 58° C., 60° C., 65° C., 70° C., or 75° C. In some embodiments, the solution is at a temperature of about 10° C., 15° C., 20° C., 25° C., 30° C., 37° C., 40° C., 42° C., 50° C., 55° C., 58° C., 60° C., 65° C., 70° C., or 75° C.

In some embodiments, the solution is compatible with DNA amplification. For example, the solution can contain one or more oligonucleotide amplification primers, dNTPs, and a DNA-dependent DNA polymerase. In some embodiments, the solution contains a cDNA template, derived from the RNA, for amplification or quantitative detection. In some cases, the RNA is RNA that has been degraded by an RNase that recognizes and digests RNA in an RNA:DNA hybrid.

The solution containing RNA contains a phosphorous or sulfur containing compound. In some cases, the phosphorous containing compound is a phosphine. In some cases, the phosphorous containing compound is a compound containing a phosphorous atom with a direct covalent bond to one, two, three, or four oxygen atoms. In some cases, the phosphorous containing compound is a phosphorus oxide. In some cases, the phosphorous containing compound is a phosphorus oxyacid (i.e., a phosphorous compound containing at least one hydroxyl group covalently bonded to the phosphorous atom). In some cases, the phosphorous containing compound is a phosphite, or phosphonate, or an organophosphate. In some cases, the organophosphate is a glycerol phosphate, such as β-glycerol phosphate (glycerol 3-phosphate), a ribose phosphate, a glucose phosphate, or a fructose phosphate. In some cases, the phosphorous containing compound is a phosphodiester. In the context of the present disclosure, the phosphorous containing compound is not a DNA or RNA oligonucleotide.

In an exemplary embodiment, the phosphorous containing compound is a phosphate. In this embodiment, the provided solution containing RNA and phosphate can, e.g., be provided by introducing into a solution a variety of different phosphate salts. For example, the phosphate can be provided into the solution as a dibasic, monobasic, or tribasic sodium or potassium phosphate salt.

In some cases, the phosphorous containing compound is a pyrophosphate, diphosphate, triphosphate, or polyphosphate containing compound. For example, the phosphorus containing compound can be pyrophosphate, diphosphate, triphosphate, polyphosphate, or a derivative thereof. Exemplary derivatives of pyrophosphate include, but are not limited to nucleoside pyrophosphates such as adenosine, inosine, uracil, guanine, thymine, or cytosine pyrophosphate. Exemplary derivatives of triphosphate include, but are not limited to nucleoside triphosphates such as adenosine, inosine, uracil, guanine, thymine, or cytosine triphosphate. In some cases, the phosphorous containing compound is a higher order polyphosphate, such as a species of the formula $[NaPO_3]_n[NaPO_3(OH)]_2$, $[KPO_3]_n[KPO_3(OH)]_2$, $[NaPO_3]_n[KPO_3(OH)]_2$, or $[KPO_3]_n[NaPO_3(OH)]_2$, wherein n is from 2 or 3 to 2000 or more.

In an exemplary embodiment, the sulfur containing compound is a sulfate. In this embodiment, the provided solution containing RNA and sulfate can, e.g., be provided by introducing into a solution a variety of different sulfate salts. For example, the sulfate can be provided into the solution as sodium sulfate, magnesium sulfate, ammonium sulfate, or a combination thereof.

The solution can contain one or more buffering agents. Exemplary buffering agents include, but are not limited to, one or more of the following: tris(hydroxymethyl)aminomethane (TRIS), N-2-hydroxyethylpiperazine-N'-2-aminoethane sulfonic acid (HEPES), N-tris-(hydroxymethyl) methyl-2-aminoethane sulfonic acid (TES), N-tris (hydroxymethyl) methylglycine (Tricene), 2-(N-morpholino)ethane sulfonic acid (MES), bis-(2-hydroxyethyl)imino-tris-(hydroxymethyl)methane (bis-tris), N-2-acetamidoiminodiacetic acid (ADA), N-(2-acetamido) iminodiacetic acid (ACES), piperazine-N,N'-bis(2-ethanesulfonic acid) (PIPS), 3-(N-morpholine)-2-hydroxypropane sulfonic acid (MOPSO), 1,3-bis[tris(hydroxymethyl)methylamino]propane(bis-tris propane), N,N-bis-(2-hydroxyethyl)-2-aminoethane sulfonic acid (BES), 3-(N-morpholine)propane sulfonic acid (MOPS), 3-[N-bis (hydroxyethyl)-amino]-2-hydroxypropane sulfonic acid (DIPSO), 3-[N-(tris-hydroxymethyl)methylamino]-2-hydroxypropane sulfonic acid (TAPSO), piperazine-N,N'bis-(2-hydroxypropane) sulfonic acid (POPSO), N-hydroxyethylpiperazine-N'-2-hydroxypropane sulfonic acid (HEPPSO), N-2-hydroxyethylpiperazine-N'-2-aminopropane sulfonic acid (EPPS), N,N-bis-(2-hydroxyethyl)glycine (bicine), N-tris(hydroxymethyl)methyl-3-aminopropane sulfonic acid (TAPS), 3-N-(α,α-dimethylhydroxuethyl)-amino-2-hydroxypropane sulfonic acid (AMPSO) and 3-N-cyclohexylamino sulfonic acid (CAPSO).

In some cases, the pH of the solution is at or between about 6 to about 8.5. In some cases, the pH of the solution containing RNA is between about 6.5 to about 8. In some cases, the pH of the solution containing RNA is between about 7 to about 8. In some cases, the pH of the solution containing RNA is at, or at about, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or 8.5. In some cases, the pH of the solution containing RNA is at a pH that eliminates or minimizes precipitation of phosphate ions, calcium ions, or calcium phosphate, if present.

In some embodiments, the phosphorous-containing or sulfur-containing compound is at a concentration of from about 0.1 mM to about 500 mM. In some embodiments, the phosphorous-containing or sulfur-containing compound is at a concentration of from about 0.5 mM to about 250 mM. In some embodiments, the phosphorous-containing or sulfur-containing compound is at a concentration of from about 0.5 mM to about 100 mM. In some embodiments, the phosphorous-containing or sulfur-containing compound is at a concentration of from about 0.5 mM to about 50 mM. In some embodiments, the phosphorous-containing or sulfur-containing compound is at a concentration of from about 0.5 mM to about 25 mM. In some embodiments, the phosphorous-containing or sulfur-containing compound is at a concentration of from about 0.5 mM to about 15 mM. In some embodiments, the phosphorous-containing or sulfur-containing compound is at a concentration of about, or of at least about, 0.1 mM, 0.2 mM, 0.3 mM, 0.4 mM, 0.5 mM, 0.6 mM, 0.7 mM, 0.8 mM, 0.9 mM, 1 mM, 1.5 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, or 22 mM, 23 mM, 24 mM, or 25 mM.

In some embodiments, the phosphorous-containing or sulfur-containing compound is sodium or potassium phosphate (monobasic, dibasic, or tribasic) at a concentration of 0.1 mM, 0.2 mM, 0.3 mM, 0.4 mM, 0.5 mM, 0.6 mM, 0.7 mM, 0.8 mM, 0.9 mM, 1 mM, 1.5 mM, 2 mM, 3 mM, 4 mM, 5 mM, 6 mM, 7 mM, 8 mM, 9 mM, 10 mM, 11 mM, 12 mM, 13 mM, 14 mM, or 15 mM. In some embodiments, the phosphorous-containing or sulfur-containing compound is provided as a sulfate salt (e.g., sodium sulfate, magnesium sulfate, ammonium sulfate) at a concentration of 1 mM, 1.5 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, or 22 mM, 23 mM, 24 mM, or 25 mM. In some embodiments, the phosphorous-containing or sulfur-containing compound is β-glycerol phosphate at a concentration of 1 mM, 1.5 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, or 22 mM, 23 mM, 24 mM, or 25 mM.

The solution containing RNA contains divalent cations. In some cases, the divalent cations are divalent magnesium cations. In some cases, the divalent cations are calcium divalent cations. In some cases, the divalent cations are manganese divalent cations. In some cases the divalent cations can be a required component of the solution for carrying out one or more enzymatic reactions, including, but not limited to DNase digestion, reverse transcription, degradation of RNA in an RNA:DNA hybrid, second strand cDNA synthesis, or nucleic acid amplification. In some cases, the solution contains two or more different divalent cations, such as magnesium and calcium divalent cations.

In some embodiments, the RNA solution contains divalent calcium cations at a concentration of from about 10 μM to about 100 mM. In some embodiments, the RNA solution contains divalent calcium cations at a concentration of from about 10 μM to about 50 mM. In some embodiments, the RNA solution contains divalent calcium cations at a concentration of from about 10 μM to about 10 mM. In some cases, the RNA solution contains divalent calcium cations at a concentration of from about 10 μM to about 10 mM. In some embodiments, the RNA solution contains divalent calcium cations at a concentration of from about 100 μM to about 10 mM. In some embodiments, the RNA solution contains divalent calcium cations at a concentration of from about 250 μM to about 10 mM. In some embodiments, the RNA solution contains divalent calcium cations at a concentration of from about 250 μM to about 5 mM. In some embodiments, the RNA solution contains divalent calcium cations at a concentration of from about 0.5 mM to about 5 mM. In some embodiments, the RNA solution contains divalent calcium cations at a concentration of, or of about, 0.01 mM, 0.02 mM, 0.03 mM, 0.04 mM, 0.05 mM, 0.075 mM, 0.1 mM, 0.2 mM, 0.3 mM, 0.4 mM, 0.5 mM, 0.6 mM, 0.7 mM, 0.8 mM, 0.9 mM, 1 mM, 1.5 mM, 2 mM, 2.5 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, or 22 mM, 23 mM, 24 mM, or 25 mM.

In some embodiments, the RNA solution contains divalent magnesium cations at a concentration of from about 10 μM to about 100 mM. In some embodiments, the RNA solution contains divalent magnesium cations at a concentration of from about 10 μM to about 50 mM. In some embodiments, the RNA solution contains divalent magnesium cations at a concentration of from about 10 μM to about 10 mM. In some embodiments, the RNA solution contains divalent magnesium cations at a concentration of from about 100 μM to about 10 mM. In some embodiments, the RNA solution contains divalent magnesium cations at a concentration of from about 250 μM to about 10 mM. In some embodiments, the RNA solution contains divalent magnesium cations at a concentration of from about 250 μM to about 5 mM. In some embodiments, the RNA solution contains divalent magnesium cations at a concentration of from about 0.5 mM to about 5 mM. In some embodiments, the RNA solution contains divalent magnesium cations at a concentration of, or of about, 0.01 mM, 0.02 mM, 0.03 mM, 0.04 mM, 0.05 mM, 0.075 mM, 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.5 mM, 2 mM, 2.5 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, or 22 mM, 23 mM, 24 mM, or 25 mM.

In some embodiments, the solution containing RNA contains calcium divalent cations at a concentration of from 10 μM to 0.5 mM, 10 μM to 1 mM, 10 μM to 2 mM, 10 μM to 3 mM, 10 μM to 4 mM, or 10 μM to 5 mM and magnesium divalent cations at a concentration of from 0.1 mM to 2.5 mM, 0.1 mM to 5 mM, 0.1 mM to 10 mM, 0.1 mM to 15 mM, 0.1 mM to 20 mM, 0.1 mM to 30 mM, 0.1 mM to 50 mM, 0.01 to 10 mM, 0.01 to 15 mM, 0.01 mM to 20 mM, 0.01 mM to 30 mM, or 0.01 mM to 50 mM. In some cases, the solution containing RNA contains calcium divalent cations at a concentration of from 0.1 mM to 1 mM and magnesium divalent cations at a concentration of from 0.5 mM to 5 mM. In some cases, the solution containing RNA contains calcium divalent cations at a concentration of about 0.5 mM and magnesium divalent cations at a concentration of about 2.5 mM.

In some embodiments, the solution containing RNA is RNase free, or substantially RNase free.

The compositions described herein include a wide array of different components (e.g., RNA, DNA, DNase, RNase H, reverse transcriptase, DNA-dependent polymerase, phosphorous or sulfur containing compound, primers, probes, and cations), parameters (e.g., time, temperature, amount, and concentration), and conditions (e.g., RNase free, free of host cell proteins, exogenous, recombinant, heterologous, digested, and protected from degradation). Such compositions include any combination of components, parameters, or conditions described herein.

All patents, patent applications, and other publications, including GenBank Accession Numbers, cited in this application are incorporated by reference in the entirety for all purposes.

EXAMPLES

The following examples are provided by way of illustration only and not by way of limitation. Those of skill in the art will readily recognize a variety of non-critical parameters that could be changed or modified to yield essentially the same or similar results.

Example 1

Increasing RNA Stability with a Phosphorous Containing Compound

Four different sets of reaction mixtures were produced, each set containing reaction mixtures with different quantities of purified RNA (100,000; 10,000; 1,000; 100; and 10 pg) (Table 1). The first set of reaction mixtures were control reaction mixtures containing RNA in water (Table 1, column 2). These control reaction mixtures were not incubated at an elevated temperature prior to reverse transcription. In the second set, RNA in DNase digestion buffer was incubated at 75° C. for 5 min prior to reverse transcription (Table 1, column 3). In the third set, 1 mM of $NaH_2PO_4$ was added to the RNA and DNase digestion buffer containing reaction mixture, and the mixture was incubated at 75° C. for 5 min prior to reverse transcription (Table 1, column 4). In the fourth set, 5 mM of $NaH_2PO_4$ was added to the RNA and DNase digestion buffer containing reaction mixture, and the mixture was incubated at 75° C. for 5 min prior to reverse transcription (Table 1, column 5). The RNA from each set of reaction mixtures was used as a template for reverse transcription of the RNA and quantitative PCR to determine the amount of resulting cDNA under otherwise identical conditions. The results are depicted in Table 1.

TABLE 1

RT-qPCR results from RQ2 assay using RNA treated with the indicated temperature and buffer conditions

| 1 | 2 RNA in $H_2O$ | | 3 RNA in DNase digestion buffer (heated at 75° C. for 5 min) | | 4 RNA in DNase digestion buffer + 1 mM $NaH_2PO_4$ (heated at 75° C. for 5 min) | | 5 RNA in DNase digestion buffer + 5 mM $NaH_2PO_4$ (heated at 75° C. for 5 min) | |
|---|---|---|---|---|---|---|---|---|
| pg RNA | Cq | ΔCq | Cq | ΔCq | Cq | ΔCq | Cq | ΔCq |
| 100,000 | 14.41 | 0 | 14.74 | 0.33 | 14.72 | 0.31 | 14.36 | −0.05 |
| 10,000 | 17.58 | 0 | 18.38 | 0.80 | 18.46 | 0.88 | 17.84 | 0.26 |
| 1,000 | 20.92 | 0 | 21.81 | 0.89 | 21.91 | 0.99 | 21.40 | 0.48 |
| 100 | 24.25 | 0 | 25.47 | 1.22 | 25.35 | 1.10 | 24.95 | 0.70 |
| 10 | 27.66 | 0 | 31.29 | 3.63 | 29.27 | 1.61 | 28.91 | 1.25 |
| 1 | 31.64 | 0 | n/a | n/a | 32.70 | 1.06 | 31.53 | −0.11 |
| Efficiency | 96.0 | | 77.4 | | 89.8 | | 93.0 | |
| $R^2$ | 0.997 | | 0.987 | | 1.000 | | 0.997 | |
| Slope | −3.421 | | −4.018 | | −3.594 | | −3.503 | |

As shown in Table 1, the use of a phosphorous-containing compound (1 mM or 5 mM $NaH_2PO_4$) significantly improved the stability of the RNA during the heat treatment. The improvement is indicated by the smaller change in Cq (ΔCq) between the control and the heated sample as compared to the ΔCq for the sample without the phosphorous-containing compound.

Example 2

Increasing RNA Stability with a Sulfur Containing Compound

Three different sets of reaction mixtures were produced, each set containing reaction mixtures with different quantities of purified RNA (100,000; 10,000; 1,000; 100; and 10 pg) (Table 2). The first set of reaction mixtures were control reaction mixtures containing RNA in water (Table 2, column 2). These control reaction mixtures were not incubated at an elevated temperature prior to reverse transcription. In the second set, RNA in DNase digestion buffer was incubated at 75° C. for 5 min prior to reverse transcription (Table 2, column 3). In the third set, 15 mM of $(NH_4)_2SO_4$ was added to the RNA and DNase digestion buffer containing reaction mixture, and the mixture was incubated at 75° C. for 5 min prior to reverse transcription (Table 2, column 4). The RNA from each set of reaction mixtures was used as a template for reverse transcription of the RNA and quantitative PCR to determine the amount of resulting cDNA under otherwise identical conditions. The results are depicted in Table 2.

TABLE 2

RT-qPCR results from RQ2 assay using RNA treated with the indicated temperature and buffer conditions

| 1 | 2 RNA in $H_2O$ | | 3 RNA in DNase digestion buffer (heated at 75° C. for 5 min) | | 4 RNA in DNase digestion buffer + 15 mM $(NH_4)_2SO_4$ (heated at 75° C. for 5 min) | |
|---|---|---|---|---|---|---|
| pg RNA | Cq | ΔCq | Cq | ΔCq | Cq | ΔCq |
| 100,000 | 16.67 | 0 | 17.26 | 0.59 | 16.47 | −0.20 |
| 10,000 | 20.22 | 0 | 21.02 | 0.79 | 20.10 | −0.12 |
| 1,000 | 23.66 | 0 | 24.58 | 0.92 | 23.48 | −0.18 |
| 100 | 26.72 | 0 | 28.43 | 1.71 | 27.87 | 1.15 |

TABLE 2-continued

RT-qPCR results from RQ2 assay using RNA treated with the indicated temperature and buffer conditions

| 1 | 2 RNA in $H_2O$ | | 3 RNA in DNase digestion buffer (heated at 75° C. for 5 min) | | 4 RNA in DNase digestion buffer + 15 mM $(NH_4)_2SO_4$ (heated at 75° C. for 5 min) | |
|---|---|---|---|---|---|---|
| pg RNA | Cq | ΔCq | Cq | ΔCq | Cq | ΔCq |
| 10 | 30.89 | 0 | n/a | n/a | n/a | n/a |
| 1 | 32.64 | 0 | n/a | n/a | n/a | n/a |
| Efficiency | 101.6 | | 86.1 | | 84.5 | |
| $R^2$ | 0.989 | | 1.000 | | 0.996 | |
| Slope | −3.284 | | 3.707 | | −3.759 | |

As shown in Table 2, the use of a sulfur-containing compound (15 mM $(NH_4)_2SO_4$) significantly improved the stability of the RNA during the heat treatment. The improvement is indicated by the smaller change in Cq (ΔCq) between the control and the heated sample as compared to the ΔCq for the sample without the sulfur-containing compound.

Example 3

Increasing RNA Stability with a Phosphorous Containing Compound

Figure 1B:
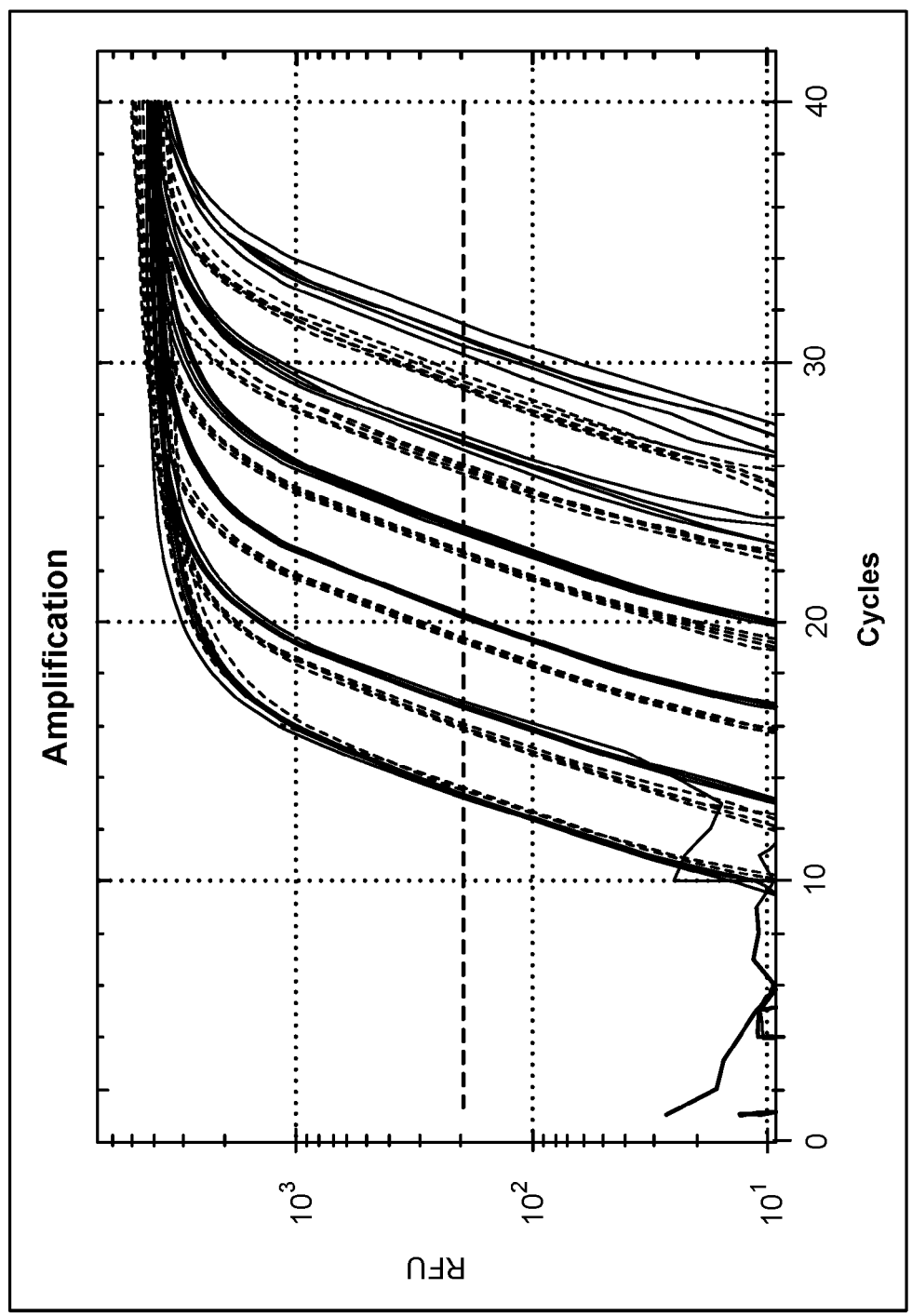
FIG. 1B: depicts real-time amplification results from a cDNA template derived from an RNA sample that is subject to various conditions. The addition of 5 mM β-glycerol phosphate (BGP) stabilizes the RNA during the heat treatment, resulting in less Cq delay in comparison to the solution of FIG. 1A.
Figure 1C:
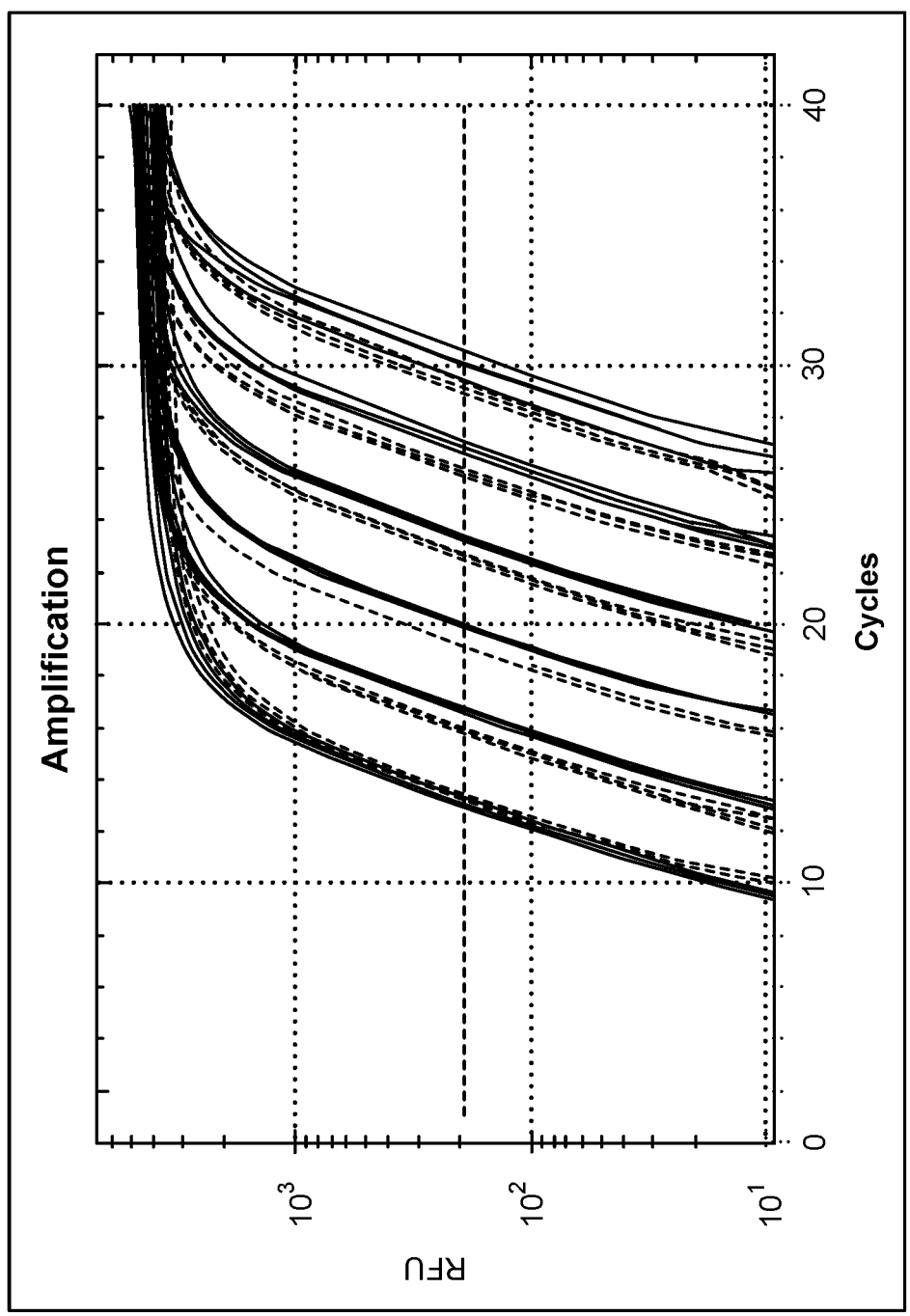
FIG. 1C: depicts real-time amplification results from a cDNA template derived from an RNA sample that is subject to various conditions. 10 mM BGP further stabilizes the RNA and reduces heat-induced Cq delay. The results of this experiment are further summarized in Table 3 of Example 3.

Four different sets of reaction mixtures were produced, each set containing reaction mixtures with different quantities of purified RNA (1,000,000; 100,000; 10,000; 1,000; 100; and 10 pg) and genomic DNA (300,000; 10,000; 1,000; 100; 10; 1) as indicated in Table 3. The first set of reaction mixtures were control reaction mixtures containing genomic DNA and RNA in water (Table 3, column 2). These control reaction mixtures were not incubated at an elevated temperature prior to reverse transcription. In the second set, genomic DNA and RNA in DNase digestion buffer with DNase was incubated at 75° C. for 5 min prior to reverse transcription (Table 3, column 3). In the third and fourth sets, 5 mM, and 10 mM of β-glycerol phosphate were added to the respective sets of reaction mixtures, and the mixtures were incubated at 75° C. for 5 min prior to reverse transcription (Table 3, columns 4 and 5). The RNA from each set of reaction mixtures was used as a template for reverse transcription of the RNA and quantitative PCR to determine the amount of resulting cDNA under otherwise identical conditions. The results are depicted in Table 3 and FIGS. 1A-C.

As shown in Table 3, the use of the phosphorous-containing compound BGP significantly improved the stability of the RNA during the heat treatment. The improvement is indicated by the smaller change in Cq (ΔCq) between the control and the heated samples as compared to the ΔCq for the sample without the BGP.

TABLE 3

RT-qPCR results from an RQ2 RNA quality assay using RNA treated with the indicated temperature and buffer conditions.

| 1 | | 2 RNA in H$_2$O | | 3 RNA in DNase digestion buffer (heated at 75° C. for 5 min) | | 4 RNA in DNase digestion buffer + 5 mM BGP (heated at 75° C. for 5 min) | | 5 RNA in DNase digestion buffer + 10 mM BGP (heated at 75° C. for 5 min) | |
|---|---|---|---|---|---|---|---|---|---|
| pg gDNA | pg RNA | Cq | ΔCq | Cq | ΔCq | Cq | ΔCq | Cq | ΔCq |
| 300,000 | 1,000,000 | 13.17 | 0 | 13.20 | 0.03 | 13.26 | 0.09 | 13.17 | 0 |
|  |  | 13.35 | 0 | 13.16 | −0.19 | 13.28 | −0.07 | 13.12 | −0.23 |
| 10,000 | 100,000 | 15.86 | 0 | 16.88 | 1.02 | 16.77 | 0.91 | 16.66 | 0.80 |
|  |  | 16.03 | 0 | 16.70 | 0.67 | 16.79 | 0.76 | 16.56 | 0.53 |
| 1,000 | 10,000 | 19.20 | 0 | 20.16 | 0.96 | 20.19 | 0.99 | 20.03 | 0.83 |
|  |  | 19.24 | 0 | 20.25 | 1.01 | 20.19 | 0.95 | 20.00 | 0.76 |
| 100 | 1,000 | 22.62 | 0 | 23.65 | 1.03 | 23.56 | 0.94 | 23.24 | 0.72 |
|  |  | 22.58 | 0 | 23.51 | 0.93 | 23.41 | 0.83 | 23.28 | 0.70 |
| 10 | 100 | 25.75 | 0 | 27.31 | 1.56 | 27.01 | 1.26 | 26.88 | 1.13 |
|  |  | 26.03 | 0 | 27.41 | 1.38 | 26.71 | 0.68 | 26.61 | 0.58 |
| 1 | 10 | 29.32 | 0 | 34.11 | 4.79 | 30.98 | 1.66 | 29.69 | 0.37 |
|  |  | 29.02 | 0 | 32.18 | 3.16 | 30.56 | 1.54 | 30.26 | 1.24 |
| Efficiency |  | 104.3 |  | 84.9 |  | 94.6 |  | 98.2 |  |
| R$^2$ |  | 0.998 |  | 0.988 |  | 0.998 |  | 0.999 |  |
| Slope |  | −3.222 |  | −3.745 |  | −3.458 |  | −3.637 |  |

What is claimed is:

1. A method of protecting RNA from degradation in a solution, said method comprising:
   providing a solution comprising:
   i. water;
   ii. RNA, wherein the RNA is purified away from endogenous host proteins of a cell or tissue from which the RNA is derived;
   iii. divalent cations;
   iv. a DNase enzyme, wherein the DNase enzyme is an active DNase enzyme that is exogenous to the cell or tissue from which the RNA is purified; and
   v. a phosphorous-containing compound selected from the group consisting of phosphate, glycerol phosphate, glucose phosphate, ribose phosphate, and pyrophosphate;
   incubating the solution at a temperature of at 40° C., wherein the incubating the solution at the temperature of at least 40° C. comprises inactivating the DNase enzyme,
   wherein the RNA is protected from degradation as compared to an RNA in an aqueous solution that contains the divalent cations but does not contain the phosphorous-containing compound.

2. The method of claim 1, wherein the providing comprises purifying RNA from the cell or tissue.

3. The method of claim 1, wherein the DNase enzyme is at a concentration of from 0.01 U/μL to 0.2 U/μL.

4. The method of claim 1, wherein the DNase enzyme is a recombinant DNase enzyme.

5. The method of claim 1, wherein before the incubating the solution at a temperature of at least 40° C., the solution comprises DNA, wherein the DNA is derived from a cell or tissue and the RNA is derived from the same cell or tissue, and the method comprises incubating the solution under conditions suitable for performing a DNase reaction, thereby degrading the DNA.

6. The method of claim 5, wherein the DNA in the solution before the DNase reaction is performed is at a concentration of less than 50 ng/μL.

7. The method of claim 1, wherein after incubating the solution at a temperature of at least 40° C., the method comprises quantifying the RNA in the solution.

8. The method of claim 1, wherein the phosphorous-containing compound is at a concentration of 5, mM, 10 mM, or 15 mM.

9. The method of claim 1, wherein the solution comprises magnesium cations and calcium cations.

10. The method of claim 9, wherein the calcium is at a concentration of from 10 µM to 1 mM and the magnesium is at a concentration of from 0.1 mM to 10 mM.

11. An aqueous solution comprising:
   i. water;
   ii. RNA, wherein the RNA is purified away from endogenous host proteins of a cell or tissue from which the RNA is derived;
   iii. divalent cations;
   iv. a DNase enzyme, wherein the DNase enzyme is an active DNase enzyme that is exogenous to the cell or tissue from which the RNA is purified; and
   v. a phosphorous-containing compound selected from the group consisting of phosphate, glycerol phosphate, glucose phosphate, ribose phosphate, and pyrophosphate
   wherein the RNA is protected from degradation as compared to an RNA in an aqueous solution that contains the divalent cations but does not contain the phosphorous-containing compound.

12. The solution of claim 11, wherein the RNA is at a concentration of from 0.1 pg/mL to 500 µg/mL.

13. The solution of claim 11, wherein the DNase enzyme is at a concentration of from 0.01 U/µL to 0.2 U/µL.

14. The solution of claim 11, wherein the DNase enzyme is a recombinant DNase enzyme.

15. The solution of claim 11, wherein the solution further comprises DNA.

16. The solution of claim 15, wherein the DNA is DNase digested.

17. The solution of claim 15, wherein the DNA in the solution is at a concentration of less than 50 ng/µL.

18. The solution of claim 15, wherein the DNA is genomic DNA and is derived from a cell or tissue and the RNA is derived from the same cell or tissue.

19. The solution of claim 11, wherein the solution is at a temperature of at least 40° C.

20. The solution of claim 11, wherein the phosphorous-containing compound is at a concentration of 5 mM, 10 mM, or 15 mM.

21. The solution of claim 11, wherein the solution comprises magnesium cations and calcium cations.

22. The solution of claim 21, wherein the calcium is at a concentration of from 10 µM to 1 mM and the magnesium is at a concentration of from 0.1 mM to 10 mM.

23. The solution of claim 11, wherein the solution is RNase free.

* * * * *

UNITED STATES PATENT AND TRADEMARK OFFICE
CERTIFICATE OF CORRECTION

PATENT NO.        : 9,896,682 B2
APPLICATION NO.   : 15/063139
DATED             : February 20, 2018
INVENTOR(S)       : Xiao-Song Gong and Cindy Wan Page 1 of 1

It is certified that error appears in the above-identified patent and that said Letters Patent is hereby corrected as shown below:

In the Claims

In Claim 1, Column 28, Line 16, please insert --least-- between "at" and "40° C".
In Claim 8, Column 28, Line 2, please delete the "," between "5" and "mM".

Signed and Sealed this
Thirtieth Day of October, 2018

Andrei Iancu
*Director of the United States Patent and Trademark Office*